(12) United States Patent
Boy et al.

(10) Patent No.: US 8,728,762 B2
(45) Date of Patent: *May 20, 2014

(54) FERMENTATIVE PRODUCTION OF ORGANIC COMPOUNDS

(75) Inventors: Matthias Boy, Langen (DE); Stephan Freyer, Neustadt (DE)

(73) Assignee: BASF SE (DE)

( * ) Notice: Subject to any disclaimer, the term of this patent is extended or adjusted under 35 U.S.C. 154(b) by 1195 days.

This patent is subject to a terminal disclaimer.

(21) Appl. No.: 12/095,130

(22) PCT Filed: Nov. 27, 2006

(86) PCT No.: PCT/EP2006/068928
§ 371 (c)(1),
(2), (4) Date: May 28, 2008

(87) PCT Pub. No.: WO2007/060235
PCT Pub. Date: May 31, 2007

(65) Prior Publication Data
US 2008/0254515 A1 Oct. 16, 2008

(30) Foreign Application Priority Data
Nov. 28, 2005 (DE) .......................... 10 2005 056 667

(51) Int. Cl.
| C12P 21/04 | (2006.01) |
| C12P 19/14 | (2006.01) |
| C12P 19/02 | (2006.01) |
| C12P 13/04 | (2006.01) |
| C12P 13/08 | (2006.01) |
| C12P 13/00 | (2006.01) |
| C12P 7/64 | (2006.01) |
| C12P 7/56 | (2006.01) |
| C12P 7/48 | (2006.01) |
| C12P 7/14 | (2006.01) |
| C12N 1/00 | (2006.01) |
| C12N 1/20 | (2006.01) |

(52) U.S. Cl.
USPC ............ 435/71.1; 435/99; 435/105; 435/106; 435/115; 435/128; 435/134; 435/139; 435/144; 435/162; 435/243; 435/252.3

(58) Field of Classification Search
USPC .......... 435/71.1, 99, 105, 106, 115, 128, 134, 435/139, 144, 162, 243, 252.3
See application file for complete search history.

(56) References Cited

U.S. PATENT DOCUMENTS

| 3,787,587 A | 1/1974 | Weber |
| 4,306,023 A | 12/1981 | Crombie |
| 4,963,486 A * | 10/1990 | Hang .............................. 435/139 |
| 5,503,750 A | 4/1996 | Russo, Jr. et al. |
| 7,820,419 B2 * | 10/2010 | Smith et al. .................... 435/161 |
| 2002/0079268 A1 | 6/2002 | Caboche et al. |
| 2004/0063184 A1 * | 4/2004 | Grichko .......................... 435/161 |
| 2008/0299606 A1 * | 12/2008 | Pompejus et al. ............... 435/67 |
| 2008/0318287 A1 * | 12/2008 | Boy et al. ......................... 435/115 |
| 2009/0162892 A1 * | 6/2009 | Pompejus et al. ............... 435/67 |
| 2009/0226571 A1 * | 9/2009 | Freyer et al. .................... 426/61 |

FOREIGN PATENT DOCUMENTS

| CN | 1173541 | 2/1998 | |
| CN | 1218111 | 6/1999 | |
| CN | 1266102 | 9/2000 | |
| CN | 1321772 A | 11/2001 | |
| DE | 3146558 A1 | 6/1983 | |
| DE | 37 31 293 | 4/1989 | |
| DE | 19519270 A1 | 12/1996 | |
| DE | 2566475 A1 * | 12/2005 | ............... C12P 7/46 |
| EP | 1205557 | 5/2002 | |
| JP | 56-169594 | 12/1981 | |
| JP | 57159500 | 10/1982 | |
| JP | 2001-072701 | 3/2001 | |
| JP | 2001-309751 * | 6/2001 | ............... A23K 1/16 |
| JP | 2001 275693 | 10/2001 | |
| JP | 2001-309751 | 11/2001 | |
| JP | 2003-164265 A | 6/2003 | |
| JP | 2003-259892 A | 9/2003 | |
| NL | 8302229 | 1/1985 | |
| WO | WO-02/077252 A1 | 10/2002 | |
| WO | WO-2004/113551 A1 | 12/2004 | |
| WO | WO-2005/116228 | 12/2005 | |
| WO | WO-2007/028804 | 3/2007 | |

OTHER PUBLICATIONS

"Getreide," [Grain] ROMPP Online, version 3.9, (German language) last accessed Nov. 24, 2010.

(Continued)

Primary Examiner — Ganapathirama Raghu
(74) Attorney, Agent, or Firm — Novak Druce Connolly Bove + Quigg LLP

(57) ABSTRACT

The invention relates to a method for producing at least one organic compound comprising at least 3 C-atoms or at least 2 C-atoms and at least 1 N-atom by fermentation. Said method comprises the following steps: i) a starch source is ground in order to obtain a grinding material which contains at least one part of the non-starch containing solid components of the starch source; ii) the grinding material is suspended in an aqueous liquid in an amount such that the dry mass content in the suspension is at least 45 wt. %, iii) the starch component is hydrolysed in the grinding material by liquefying and optionally, subsequently, sweetening, in order to obtain an aqueous medium M, which contains the hydrolysed starch components and at least one part of the non-starch containing solid components of the starch source, is obtained; and iv) the aqueous substance M obtained in step iii) is used for fermentation in order to cultivate a micro-organism which is capable of over-producing the organic compound; the suspension obtained in step ii) is heated in step iii) by introducing vapor into the suspension, in order to obtain temperatures greater than the pasting temperature of the starch obtained in the grinding materials.

17 Claims, No Drawings

(56) References Cited

OTHER PUBLICATIONS

"Begleitalkohol," [by-product formation during alcohol fermentation] Wikipedia.de entry, (German language) last accessed Dec. 13, 2010.

"Bioethanol-Produktionsverfahren," [Bioethanol production methods] Crop Energies AG, (German language), http://www.cropenergies.com/de/Bioethanol/Produktionsverfahren, page last updated Aug. 6, 2009.

"Lehrbuch der angewandten Mikrobiologie," p. 223,—"Kohlenhydrat-Antibiotika," Crueger et al., Akademische Verlagsgesellschaft Wiesbaden 1982.

Pfefferle et al., "Biotechnological Manufacture of Lysine", *Advances in Biochemical Engineering/Biotechnology*, vol. 79 (2003), 59-112.

Beukema et al., "Production of fermentation syrups by enzymatic hydrolysis of potatoes", Symp. Biotechnol. Res. Neth. (1983), 6.

Mersmann et al, "Selection and Design of Aerobic Bioreactors", Ehem. Eng. Technol. 13 (1990), 357-370.

Botterbrodt et al., "Handbuch Mehl-und Schälmüllerei", vol. 3, (2008), pp. 49-50, pp. 316-317, pp. 320-321.

* cited by examiner

FERMENTATIVE PRODUCTION OF ORGANIC COMPOUNDS

CROSS-REFERENCE TO RELATED APPLICATIONS

This application is a national phase of PCT/EP2006/068928, filed on Nov. 27, 2006, which claims priority to DE 10 2005 056 667.7, filed Nov. 28, 2005, the entire contents of all are hereby incorporated by reference.

The present invention relates to the fermentative production of organic compounds having at least 3 C atoms or having at least 2 C atoms and at least 1 N atom using, for culturing the microorganisms, a sugar-containing medium which comprises at least part of the nonstarchy solid constituents of the starch feedstock.

Sugar-containing liquid media are a basic nutrient source for a multiplicity of fermentative processes; the sugar components which are present in the media are metabolized by the microorganisms employed, giving rise to organic products of value. The range of microbial metabolites thus prepared, i.e. organic compounds, comprises for example low-molecular-weight volatile compounds such as ethanol, nonvolatile metabolites such as amino acids, vitamins and carotenoids, and a multiplicity of further substances.

Depending on the various process conditions, different carbon feedstocks are exploited for such generally known microbial fermentative processes. They extend from pure sucrose via beet, and sugarcane molasses to what are known as high-test molasses (inverted sugarcane molasses) to glucose from starch hydrolyzates. Moreover, acetic acid and ethanol are mentioned as cosubstrates which can be employed on an industrial scale for the biotechnological production of L-lysine (Pfefferle et al., Biotechnological Manufacture of Lysine, Advances in Biochemical Engineering/Biotechnology, Vol. 79 (2003), 59-112).

Based on the abovementioned carbon feedstocks, various methods and procedures for the sugar-based, fermentative production of microbial metabolites are established. Taking L-lysine as an example, these are described for example by Pfefferle et al. (loc. cit.) with regard to strain development, process development and industrial production.

An important carbon feedstock for the microorganism-mediated fermentative production of microbial metabolites is starch. The latter must first be liquefied and saccharified in preceding reaction steps before it can be exploited as carbon feedstock in a fermentation. To this end, the starch is usually obtained in pre-purified form from a natural starch feedstock such as potatoes, cassava, cereals, for example wheat, corn, barley, rye, triticale or rice, and subsequently enzymatically liquefied and saccharified, where after it is employed in the actual fermentation for producing the desired metabolites.

In addition to the use of such pre-purified starch feedstocks, the use of non-pretreated starch feedstocks for the preparation of carbon feedstocks for the fermentative production of microbial metabolites has also been described. Typically, the starch feedstocks are initially comminuted by grinding. The millbase is then subjected to liquefaction and saccharification. Since this millbase naturally comprises, besides starch, a series of nonstarchy constituents which may adversely affect the fermentation, these constituents are usually removed prior to fermentation. The removal can be effected either directly after grinding (WO 02/077252; JP 2001-072701; JP 56-169594; CN 1218111), after liquefaction (WO 02/077252; CN 1173541) or subsequently to saccharification (CN 1266102; Beukema et al.: Production of fermentation syrups by enzymatic hydrolysis of potatoes; potato saccharification to give culture medium (Conference Abstract), Symp. Biotechnol. Res. Neth. (1983), 6; NL8302229). However, all variants involve the use of a substantially pure starch hydrolyzate in the fermentation.

Novel processes for fermentative production of organic compounds comprise in particular a purification of the starch feedstocks prior to fermentation, for example the purification of liquefied and saccharified starch solutions (JP 57159500), or provide methods which are intended to make possible the preparation of fermentation media from renewable resources (EP 1205557).

Unprocessed starch feedstocks, in contrast, are known to be applied on a large scale in the fermentative production of bioethanol. Here, the starch feedstocks, usually whole cereal grains, are first subjected to dry milling, and the starch constituent of the starch feedstock is subsequently hydrolyzed using enzymes. Here, the hydrolysis can be carried out batchwise, for example in stirred vessels, or else continuously, for example in jet cookers. Descriptions of suitable processes can be found for example in "The Alcohol Textbook—A reference for the beverage, fuel and industrial alcohol industries", Jaques et al. (Ed.), Nottingham Univ. Press 1995, ISBN 1-8977676-735, Chapter 2, pp. 7 to 23, and in McAloon et al., "Determining the cost of producing ethanol from corn starch and lignocellulosic feedstocks", NREL/TP-580-28893, National Renewable Energy Laboratory, October 2000.

Since in the fermentative production of bioethanol the product of value is obtained by distillation, the use of starch feedstocks from the dry-milling process in non-prepurified form does not constitute a serious problem. However, when using a dry-milling method for the production of other microbial metabolites, the solids stream which is introduced into the fermentation via the sugar solution is problematic since it not only may have an adverse effect on the fermentation, for example regarding the oxygen transfer rate or the oxygen requirement of the microorganisms employed (cf., in this context, Mersmann, A. et al.: Selection and Design of Aerobic Bioreactors, Chem. Eng. Technol. 13 (1990), 357-370), but may also considerably complicate the subsequent workup.

Moreover, as a result of the introduction of solids, the viscosity of the suspension may reach a critical value even whilst the starch-containing suspension is being prepared, as a result of which for example a suspension containing more than 30% by weight of corn meal is no longer homogenously miscible in water (Industrial Enzymology, 2nd Ed., T. Godfrey, S. West, 1996). This limits the glucose concentration in traditional procedures. With regard to the fermentative production of bioethanol, this is no longer relevant in as far as higher concentrations can anyway not be converted in a meaningful manner as the result of the toxicity of the products to the yeasts employed for the fermentation.

Feeding to the fermentation sugar-containing media with a low sugar concentration is in principle disadvantageous in the fermentative production of organic metabolites other than ethanol because this procedure results in a disproportionate dilution of the fermentation liquor and, as a consequence, the achievable final concentration of the products of interest is reduced which firstly results in increased costs when these products are obtained from the fermentation medium and secondly the space-time yield decreases. These considerations are of importance in particular in the case where a starch hydrolyzate which is produced for a large-volume bioethanol production and which traditionally has low sugar or glucose concentrations of up to approximately 30 or 33% by weight is intended to be fed in part to a lower-volume secondary fermentation for the production of other chemicals.

Owing to these difficulties and limitations, dry-milling methods as they have been employed widely for the production of bioethanol have as yet remained without particular economical importance in the fermentative production of microbial metabolites other than ethanol.

To date, attempts to apply the dry-milling concept and the advantages which exist in principle in connection with this method, to the industrial-scale production of microbial metabolites have only been described using Cassava as starch feedstock. Thus, while JP 2001/275693 describes a method for the fermentative production of amino acids in which peeled cassava tubers which have been ground in the dry state are employed as starch feedstock, it is necessary, to carry out the process, to adjust the particle size of the millbase to ≤150 µm. In the filtration step which is employed for this purpose, parts of the millbase, including non-starch-containing constituents, are removed before the starch present is liquefied/saccharified and subsequently fermented. In this process, moderate sugar concentrations are obtained. A similar process is described in JP 2001/309751 for the production of an amino-acid-containing feed additive.

Increased sugar concentrations in the liquid medium employed for the fermentation can be achieved by using a millbase, for the saccharification, which largely comprises the solid, nonstarchy constituent of the starch feedstock, by the process described in WO 2005/116228 (PCT/EP2005/005728) of the applicant company. Surprisingly, it has emerged that the solid, nonstarchy constituents which are present in the starch feedstock need not be removed before the fermentation. A similar process using starch feedstock selected among cereal grains is described in PCT/EP2006/066057 (earlier patent application DE 10 2005 042 541.0) of the applicant company. However, this process is comparatively complicated for the continuous provision of sugar-containing media with a high sugar concentration.

It is an object of the present invention to provide another process for the fermentative production of organic compounds which requires no, at least no complete, previous removal of the nonstarchy solid constituents present in the starch feedstock. In particular, the process should make possible a continuous hydrolysis of the starch component of the starch feedstock. Moreover, it was to be distinguished by easy handling of the media used and by their unproblematic use in the fermentation process. In particular, the process was to allow the use of cereals as starch feedstock.

Surprisingly, it has been found that a fermentative process for the production of organic compounds can be carried out efficiently despite the inherently high introduction of solids when the sugar which is required for the fermentation is provided in the form of an aqueous medium obtainable by
i) milling a starch feedstock, thus obtaining a millbase which comprises at least part of the nonstarchy solid constituents of the starch feedstock;
ii) suspending the millbase in an aqueous liquid in such an amount that a dry-matter content in the suspension of at least 45% by weight results,
iii) hydrolyzing the starchy constituent in the millbase by liquefaction and, if appropriate, subsequent saccharification, whereby an aqueous medium M is obtained which comprises the hydrolyzed starchy constituents of the starch feedstock and at least part of the nonstarchy solid constituents of the starch feedstock, where the hydrolysis comprises heating the suspension of the millbase by introducing steam into the suspension at temperatures above the gelatinization temperature of the starch present in the millbase.

The invention thus provides a process for the fermentative production of at least one organic compound having at least 3 C atoms or having at least 2 C atoms and at least one 1 N atom, comprising, in addition to the steps i) and ii), the following steps:
iii) hydrolysis of the starchy constituent in the millbase by liquefaction and, if appropriate, subsequent saccharification, which gives an aqueous medium M which comprises the hydrolyzed starchy constituents of the starch feedstock and at least part of the nonstarchy solid constituents of the starch feedstock; and
iv) use of the aqueous medium M obtained in step iii) in a fermentation to culture a microorganism which is capable of overproducing the organic compound;
where, in step iii), the suspension obtained in step ii) is heated at temperatures above the gelatinization temperature of the starch present in the millbase by introducing steam into the suspension.

Despite the high dry matter content in the suspension employed for the hydrolysis, the hydrolysis can be carried out without problems in the manner according to the invention, and, accordingly, high concentrations of metabolizable sugars are obtained. Surprisingly, it does not matter whether the sugar after the hydrolysis is present in the form of mono- or of disaccharides or in the form of oligosaccharides (=dextrins). Surprisingly, the high content of solid, nonstarchy constituents of the starch feedstock in the medium obtained does not interfere with the fermentation. Moreover, viscosity problems as they can arise upon liquefaction of the starch feedstock at higher millbase concentrations are largely avoided as the result of the process according to the invention. As the result of the high concentration of metabolizable sugars in the fermentation medium, which is the result of the high dry matter content, the medium can be employed particularly advantageously in the feed phase of the fermentation, whereby an undesired dilution is largely avoided or at least markedly reduced. Naturally, the medium M which is obtainable in accordance with the invention is suitable as sugar source in the batch phase of the fermentation.

Here and hereinbelow, the terms "starch component" and "starchy constituent" are used synonymously.

With regard to the aqueous medium M obtained in step iii), the terms "aqueous medium", "liquid medium" and "aqueous sugar-containing liquid" are used synonymously.

Here and hereinbelow, the term "liquefaction" means the hydrolytic degradation of starch to give oligosaccharides, in particular dextrins.

Here and hereinbelow, the terms "saccharification" or "to saccharify" mean the hydrolysis of dextrins to give monosaccharides, in particular to give monosaccharides such as glucose. As a consequence, a "saccharifying enzyme" is understood as meaning an enzyme which hydrolyzes dextrins to give monosaccharides.

Here and hereinbelow, the term "dextrin" means oligosaccharides obtained as the result of the hydrolytic degradation of starch, which oligosaccharides consist, as a rule, of 3 to 18, in particular 6 to 12, monosaccharide units, in particular of glucose units.

The terms "glucose equivalent content" and "sugar concentration" refers to the total concentration of mono-, di- and oligosaccharides in the medium which is potentially available for a fermentation. The term "glucose equivalents" also comprises the metabolizable sugars or sugar units which are other than glucose.

Here and hereinbelow, the terms "overproducing" or "overproduction" are used to refer to a microorganism in order to identify its characteristic of producing one or more of its metabolites in an amount which exceeds the amount required for the multiplication of the microorganism, which results in an accumulation in the fermentation medium, it being possible for the accumulation to take place outside or inside the cells.

Suitable as starch feedstock for the milling are, mainly, dry cereal or seeds where the starch amounts to at least 40% by weight and preferably at least 50% by weight in the dried state. They are found in many of the cereal plants which are currently grown on a large scale, such as maize, wheat, oats, barley, rye, triticale, rice, sugar beet, potatoes, cassava and various sorghum and millet species, for example sorgo and milo. The starch feedstock is preferably selected from among cereal, especially preferably among maize, rye, triticale and wheat kernels. In principle, the process according to the invention can also be carried out with similar starch feedstocks such as, for example, a mixture of various starch-containing cereal or seeds.

To prepare the sugar-containing liquid medium, the starch feedstock in question is milled in step i), with or without addition of liquid, for example water, preferably without addition of liquid. It is also possible to combine dry milling with a subsequent wet-milling step.

Apparatuses which are typically employed for dry milling are hammer mills, rotor mills or roller mills; those which are suitable for wet grinding are paddle mixers, agitated ball mills, circulation mills, disk mills, annular chamber mills, oscillatory mills or planetary mills. In principle, other mills are also suitable. The amount of liquid required for wet grinding can be determined by the skilled worker in routine experiments. It is usually adjusted in such a way that the dry matter content is in the range of from 10 to 20% by weight.

Milling brings about a particle size which is suitable for the subsequent process steps. In this context, it has proved advantageous when the millbase obtained in the milling step, in particular the dry milling step, in step i) has flour particles, i.e. particulate constituents, with a particle size in the range of from 100 to 630 µm in an amount of from 30 to 100% by weight, preferably 40 to 95% by weight and especially preferably 50 to 90% by weight. Preferably, the millbase obtained comprises 50% by weight of flour particles with a particle size of more than 100 µm. As a rule, at least 95% by weight of the milled flour particles have a particle size of less than 2 mm. In this context, the particle size is measured by means of screen analysis using a vibration analyzer. In principle, a small particle size is advantageous for obtaining a high product yield. However, an unduly small particle size may result in problems, in particular problems due to clump formation/agglomeration, when the millbase is slurried during liquefaction or processing, for example during drying of the solids after the fermentation step.

Usually, flours are characterized by the extraction rate or by the flour grade, whose correlation with one another is such that the characteristic of the flour grade increases with increasing extraction rate. The extraction rate corresponds to the amount by weight of the flour obtained based on 100 parts by weight of millbase applied. While, during the milling process, pure, ultrafine flour, for example from the interior of the cereal kernel, is initially obtained, with further milling, i.e. with increasing extraction rate the amount of crude fiber and husk content in the flour increases and the starch content decreases. The extraction rate is therefore also reflected in what is known as the flour grade, which is used as a figure for classifying flours, in particular cereal flours, and which is based on the ash content of the flour (known as ash scale). The flour grade or type number indicates the amount of ash (minerals) in mg which is left behind when 100 g of flour solids are incinerated. In the case of cereal flours, a higher type number means a higher extraction rate since the core of the cereal kernel comprises approximately 0.4% by weight of ash, while the husk comprises approximately 5% by weight of ash. In the case of a lower extraction rate, the cereal flours thus consist predominantly of the comminuted endosperm, i.e. the starch content of the cereal kernels; in the case of a higher extraction rate, the cereal flours also comprise the comminuted, protein-containing aleurone layer of the grains; in the case of coarse meal, they also comprise the constituents of the protein-containing and fat-containing embryo and of the seed husks, which comprise raw fiber and ash. For the purposes of the invention, flours with a high extraction rate, or a high type number, are preferred in principle. If cereal is employed as starch feedstock, it is preferred that the intact kernels together with their husks are milled and processed, if appropriate after mechanical removal of the embryo and the husks beforehand.

In accordance with the invention, the millbase used comprises at least some, preferably at least 20% by weight, in particular at least 50% by weight, specifically at least 90% by weight and very specifically at least 99% by weight of the nonstarchy solid constituents which are present in the milled cereal kernels, corresponding to the extraction rate. Based on the starchy constituents of the millbase (and thus on the amount of metabolizable sugar in the medium M), the nonstarchy solid constituents in the millbase preferably amount to at least 10% by weight and in particular at least 15% by weight, for example between 15 and 75% by weight and specifically between 20 and 60% by weight.

Subsequently, the millbase in step ii) is mixed with an aqueous liquid, for example fresh water, recirculated process water, for example from subsequent fermentation, or with a mixture of these liquids, giving an aqueous suspension. This procedure is frequently also referred to as slurrying.

As a rule, such an amount of the starch feedstock, or of the millbase, will be mixed with the aqueous liquid that the suspension obtained has a dry matter content of at least 45% by weight, frequently at least 50% by weight, in particular at least 55% by weight, specifically at least 60% by weight, for example 45 to 80% by weight, preferably 50 to 75% by weight, in particular 55 to 70% by weight and specifically 60 to 70% by weight.

In principle, it is possible to preheat the aqueous fluid used for suspending the solid millbase to a moderately increased temperature, for example in the range of from 40 to 70° C. It is preferred that the temperature of the liquid is chosen in such a way that the suspension obtained has a temperature below the gelatinization temperature, preferably at least 5 K below the gelatinization temperature of the starch. Preferably, the temperature of the suspension will not exceed 60° C., in particular 55° C.

Suspending the particulate millbase in the aqueous liquid can be accomplished either batchwise or else continuously in the apparatuses conventionally used for this purpose, for example batchwise in stirred mixers or in continuously operated mixing devices for mixing solids with liquids, for example in mixers which operate by the rotor/stator principle.

To carry out the hydrolysis, the aqueous suspension comprising the millbase is first heated to a temperature above the gelatinization temperature of the starch present in the starch feedstock or the millbase by introducing steam. The temperature required for the specific starch for this purpose is known to a person skilled in the art (see "The Alcohol Textbook—A reference for the beverage, fuel and industrial alcohol industries", chapter 2, p. 11, which has been mentioned at the outset) or can be determined by him by routine experimentation. Typically, the suspension will be heated at a temperature which is at least 10 K and in particular at least 20 K, for example 10 to 100 K, in particular 20 to 80 K, above the gelatinization temperature in question. In particular, the suspension is heated to temperatures in the range of from 90 to 150° C., specifically in the range of from 100 to 140° C.

The steam employed for heating the suspension is typically superheated steam with a temperature of at least 105° C., in particular at least 110° C., for example 110 to 210° C. The steam is preferably introduced into the suspension at superatmospheric pressure. Accordingly, the steam preferably has a pressure of at least 1.5 bar, for example 1.5 to 16 bar, in particular 2 to 12 bar.

As a rule, steam is introduced into the suspension in such a way that the steam is introduced into the suspension at superatmospheric pressure, preferably a superatmospheric pressure of 1 to 10 or 11 bar, in particular 1.5 to 5 bar, preferably at high speed. The result of introducing the steam is that the suspension is instantly heated to temperatures of above 90° C., that is temperatures above the gelatinization temperature.

Heating with steam is preferably carried out in a continuously operating device which is charged with the suspension continuously at a specific feed pressure which is the result of the viscosity of the suspension, the feed rate and the geometry of the device and which, in the suspension charge zone, is charged with the hot steam via an adjustable nozzle at elevated pressure based on the feed pressure. Feeding the steam at elevated pressure means that not only is the suspension heated, but also mechanical energy is introduced into the system, and this mechanical energy promotes a further comminution of the millbase particles, brings about a particularly uniform energy supply, and thus brings about especially uniform gelatinization of the granular starch particles in the millbase. These devices typically have a tubular geometry. The steam is preferably fed in along the longitudinal axis of the tubular device. As a rule, the suspension is supplied at an angle of at least 45° or at a right angle. The adjustable nozzle typically has a conical geometry which tapers in the flow direction of the steam. A needle, or a cone which is arranged on a longitudinally displaceable rod, is arranged within this nozzle. Needle, or cone, together with the cone of the nozzle, forms an aperture. By displacing the needle, or the rod, longitudinally, the size of the aperture, and thus the cross-sectional area of the nozzle end can be adjusted in a simple manner, whereby the speed at which steam is supplied can be controlled in a simple manner.

These devices are typically also equipped with a mixing tube into which the suspension is transported after the steam has been supplied and in which the suspension leaves the device. This mixing tube is usually arranged along the steam supply and perpendicular to the feed. The mixing tube and the nozzle together typically form an aperture through which the suspension is transported. As the result of this aperture, additional shear forces act on the suspension during the transport process and thus increase the supply of mechanical energy to the suspension. The mixing tube can be arranged in such a way that it is longitudinally displaceable. Displacing the mixing tube is a simple way of adjusting the size of the aperture and thus of the drop of pressure in the device.

Such devices are known from the prior art under the name jet cooker, for example the device which is shown in "The Alcohol Textbook", Chapter 2, loc. cit., FIG. 13, and commercially available, for example under the name HYDRO-HEATER® from Hydro Thermal Corp. Waukesha Wis., USA.

When reaction is carried out continuously, the suspension treated with steam is, as a rule, subsequently transferred into an after-reaction zone in order to continue the gelling of the starch constituents. Typically, a superatmospheric pressure, typically an absolute pressure of in the range of from 2 to 8 bar, prevails in the after-reaction zone. The temperatures in the after-reaction zone are typically in the range of from 90 to 150° C. The residence time in this after-reaction zone can be in the range of from 1 minute to 4 hours, depending on the temperature of the suspension. The after-reaction zones typically have a tubular or column geometry. In one embodiment, the after-reaction zone has the geometry of a vertically arranged column. Here, the suspension, once it has left the steam treatment device, is applied in the upper zone of the column and withdrawn in the lower zone. In another embodiment of the invention, the after-reaction zone has a tubular geometry.

After the suspension has left the after-reaction zone, the pressure is released, as a rule, and a liquefaction is subsequently carried out. Releasing the pressure is preferably carried out in the form of a flash evaporation in order to cool the suspension to, preferably, temperatures of below 100° C., in particular below 85° C. As a rule, the starch thus disintegrated is then liquefied in a separate reaction vessel. The liquefaction can be carried out as described above.

The liquefaction can be carried out in the customary manner. As a rule, the liquefaction in step ii) is accomplished in the presence of at least one starch-liquefying enzyme which is, as a rule, selected among α-amylases. Other enzymes which liquefy active and stable starch under the reaction conditions can also be employed.

To liquefy the starch portion in the millbase, it is possible in principle to employ all starch-liquefying enzymes, in particular α-amylases (enzyme class EC 3.2.1.1), for example the α-amylases which have been obtained from *Bacillus lichenformis* or *Bacillus staerothermophilus*, and specifically those which are used for liquefying substances obtained by dry-milling methods within the scope of the bioethanol production. Preferred enzymes are temperature-stable, i.e. they do not lose their enzymatic activity even when heated at temperatures above the gelatinization temperature. The α-amylases which are suitable for the liquefaction are also commercially available, for example from Novozymes under the name Termamyl 120 L, type L; or from Genencor under the name Spezyme. It is also possible to employ a combination of different α-amylases for the liquefaction.

Advantageously, the amounts of starch-liquefying enzyme, in particular α-amylase, are selected in such a way that a rapid and complete degradation of the starch into oligosaccharides is achieved. The total amount of starch-liquefying enzyme, in particular α-amylase, is usually in the range of from 0.002 to 3.0% by weight, preferably from 0.01 to 1.5% by weight and especially preferably from 0.02 to 0.5% by weight, based on the total amount of starch feedstock employed. The α-amylase (or the starch-liquefying enzyme used) can be initially introduced into the reaction vessel or else added during the liquefaction step.

For an optimal activity of the α-amylase (or of the starch-liquefying enzyme used), step ii) is preferably carried out—at least for some time—at a pH value within the pH optimum of the liquefying enzyme, frequently at a pH value in the weakly acidic range, preferably between 4.0 and 7.0, especially preferably between 5.0 and 6.5, where the pH is usually adjusted before or at the beginning of step ii); this pH is preferably checked during the liquefaction and, if appropriate, readjusted. The pH is preferably adjusted using dilute mineral acids such as $H_2SO_4$, $H_3PO_4$, or dilute alkali hydroxide solutions such as NaOH or KOH.

To stabilize the enzymes employed, the concentration of $Ca^{2+}$ ions may, if appropriate, be adjusted to an enzyme-specific optimum value, for example using $CaCl_2$. Suitable concentration values can be determined by the skilled worker in routine experiments. If, for example Termamyl is employed as α-amylase, it is advantageous to adjust the $Ca^{2+}$ concentration to, for example, 10 to 100 ppm, preferably 20 to 80 ppm and especially preferably approximately 30 to 70 ppm in the liquid medium, the unit ppm being based on weight and meaning g/1000 kg.

To fully degrade the starch into dextrins, the reaction mixture is held at the set temperature until the detection of starch by means of iodine or, if appropriate, another test for detecting starch is negative or at least essentially negative. If appropriate, one or more further α-amylase portions, for example in the range of from 0.001 to 0.5% by weight and preferably from 0.002 to 0.2% by weight, based on the total amount of the starch feedstock employed, may now be added to the reaction mixture.

In a preferred embodiment of the invention, at least some or all, generally at least 50%, in particular at least 80%, or else all of the starch-liquefying enzyme is added to the suspension of the millbase in the aqueous liquid before the steam heating process. In this manner, the liquefaction process already takes place while the mixture is heated to temperatures of above the gelatinization temperature. Heating with steam, and the after reaction phase, are carried out appropriately. A subsequent liquefaction step in a separate reaction vessel can be dispensed with. However, such a liquefaction step will be carried out to complete the degradation of the starch into dextrins.

This gives an aqueous starch hydrolyzate which comprises the liquefied starch portion from the millbase, typically dextrins and, if appropriate, further oligosaccharides and mono- or disaccharides, and the nonstarchy constituents of the millbase, in particular the solid, nonstarchy components of the millbase employed for the liquefaction.

This hydrolyzate can be fed directly to a fermentation for the preparation of the organic compound as the aqueous medium M. Frequently, however, a saccharification will be carried out. The saccharification can be performed in analogy with the known saccharification processes of the prior art.

The saccharification can be carried out continuously or batchwise. To this end, the liquefied medium is typically saccharified completely in a specific saccharification tank before being fed for example to a subsequent fermentation step. To this end, the aqueous product obtained after the liquefaction will be treated with an enzyme which brings about the saccharification, typically a glucoamylase, under the conditions usually employed for this purpose.

For the saccharification of the dextrins (i.e. oligosaccharides) use may be made, in principle, of all the glucoamylases (enzyme class EC 3.2.1.3), in particular glucoamylases obtained from *Aspergilus* and specifically those which are used for saccharifying materials obtained by dry-milling methods in connection with the production of bioethanol. The glucoamylases which are suitable for the saccharification are also commercially available, for example from Novozymes under the name Dextrozyme GA; or from Genencor under the name Optidex. A combination of different glucoamylases may also be used.

The saccharifying enzyme is added to the dextrin-containing hydrolyzate obtained after the liquefaction in an amount of from usually 0.001 to 5.0% by weight, preferably 0.005 to 3.0% by weight and especially preferably 0.01 to 1.0% by weight, based on the total amount of the starch feedstock employed.

As a rule, the saccharification is carried out at temperatures within the range of the temperature optimum of the saccharifying enzyme or slightly below, for example at 50 to 70° C., preferably at 60 to 65° C. The aqueous liquefaction product will preferably first be brought to these temperatures and subsequently treated with the enzyme which brings about the saccharification. It is advantageous prior to adding the saccharifying enzyme, for example the glucoamylase, to adjust the pH of the liquid hydrolyzate to a value in the optimal activity range of the enzyme employed, preferably in the range of between 3.5 and 6.0; especially preferably between 4.0 and 5.5 and very especially preferably between 4.0 and 5.0.

After addition of the saccharifying enzyme, the dextrin-containing suspension is preferably held at the temperature set for a period of, for example, from 2 to 72 hours or longer, if required, in particular from 5 to 48 hours, during which time the dextrins are saccharified to give monosaccharides. The progress of the saccharification process can be monitored by the skilled worker using known methods, for example HPLC, enzyme assays or glucose test strips. The saccharification has ended when the monosaccharide concentration no longer arises substantially or drops again.

Since millbase which comprises essentially all constituents of the starch feedstock, or at least, besides the starch, also some of the solid nonstarchy constituents, is employed for the preparation of the sugar-containing liquid medium (1) (i.e. the nonstarchy solid constituents of the starch feedstock are not fully removed), the liquid hydrolyzate obtained after liquefaction and optionally saccharification also comprises some or the whole amount of the nonstarchy solid constituents of the starch feedstock. This frequently brings about the introduction of an amount of phytate, for example from the cereal, which amount is not to be overlooked. To avoid the inhibitory effect which thus results, it is advantageous to add one or more phytases to the hydrolyzate before subjecting the latter to a fermentation step. The phytase can be added before, during or after the liquefaction if it is sufficiently stable to the respective high temperatures. Any phytases can be employed as long as their activity is in each case not more than marginally affected under the reaction conditions. Phytases used preferably have a heat stability (T50)>50° C. and especially preferably >60° C. The amount of phytase is usually from 1 to 10 000 units/kg starch feedstock and in particular 10 to 4000 units/kg starch feedstock.

To increase the overall sugar yield, or to obtain free amino acids, further enzymes, for example pullulanases, cellulases, hemicellulases, glucanases, xylanases, glucosidases or proteases, may be added during the liquefaction or during the saccharification. The addition of these enzymes can have a positive effect on the viscosity, i.e. reduced viscosity (for example by cleaving long-chain (also referred to as longer-chain) glucans and/or (arabino-)xylans), and bring about the liberation of metabolizable glucosides and the liberation of (residual) starch. The use of proteases has analogous positive effects, it additionally being possible to liberate amino acids which act as growth factors for the fermentation.

In another embodiment of the invention, no, or only a partial, saccharification will be carried out before the fermentation. In this case, the saccharification is accomplished at least in part during the fermentation, i.e. in situ. For example, a procedure can be followed in which a part of the dextrins present in the liquid medium, for example in the range of from 10 to 90% by weight and in particular in the range of from 20 to 80% by weight, based on the total weight of the dextrins (or of the original starch) is saccharified and the resulting sugar-containing medium is employed in the fermentation. A further saccharification can then be effected in situ in the fermentation medium. Moreover, the saccharification can be carried out directly in the fermenter, dispensing with a separate saccharification tank.

The in-situ saccharification can be accomplished with addition of saccharifying enzymes as described above or else in the absence of such enzymes, since many microorganisms are themselves capable of metabolizing oligosaccharides. In such a case, the dextrins are either taken up as such by the microorganism and metabolized or hydrolyzed, after a preceding saccharification, by saccharifying enzymes which are intrinsic to the strain, for example glucoamylases which are intrinsic to the strain, and then metabolized. A particularly advantageous aspect of the latter case is that the rate of the saccharification, in particular of a release of glucose, during the fermentation is adapted automatically to the requirement of the microorganisms, firstly by the amount of biomass and secondly by the expression level of the saccharifying enzymes which are intrinsic to the strain.

Advantages of the in-situ saccharification are firstly a reduced investment outlay; secondly, a delayed release of the glucose may, if appropriate, allow a higher glucose concentration to be introduced into the batch without inhibition or metabolic changes in the microorganisms employed taking place. In *E. coli*, for example, an unduly high glucose concentration leads to the formation of organic acids (acetate), while *Saccharomyces cerevisae* in such a case switches for example to fermentation, despite the presence of sufficient oxygen in aerated fermenters (Crabtree effect). A delayed release of glucose can be adjusted by controlling the glucoamylase concentration. This makes it possible to suppress the abovementioned effects, and more substrate can be introduced initially so that the dilution, which is the result of the feedstream supplied, can be reduced.

The aqueous hydrolyzate obtained after liquefaction and, if appropriate, any saccharification which has been carried out, i.e. the medium M, typically has a dry matter content of at least 45% by weight, frequently at least 50% by weight, in particular at least 55% by weight, specifically at least 60% by weight, for example 45 to 80% by weight, preferably 50 to 75% by weight, in particular 55 to 70% by weight and specifically 60 to 70% by weight. Accordingly, the aqueous medium M obtained after the hydrolysis has, as a rule, a sugar concentration—calculated as glucose equivalents—of at least 35% by weight, frequently at least 40% by weight, in particular at least 45% by weight, specifically at least 50% by weight, for example 35 to 70% by weight, in particular 40 to 65% by weight, in particular 45 to 60% by weight and specifically 50 to 60% by weight, based on the total weight of the medium M.

Depending on how the process is conducted, the glucose equivalents present in the resulting medium M are present in the form of mono- or oligosaccharides, in particular dextrins. The main components are typically monosaccharides such as hexoses and pentoses, for example glucose, fructose, mannose, galactose, sorbose, xylose, arabinose and ribose, in particular glucose or oligosaccharides of these monosaccharides. The amount of monosaccharides other than glucose in free form or as component of the oligosaccharides in the medium M can vary as a function of the starch feedstock used and the nonstarchy constituents which it comprises and can be influenced by the way in which the process is conducted, for example the disintegration of cellulose constituents by addition of celluloses. Typically, the glucose portion, in free or bound form, among the glucose equivalents of the medium M amounts to from 50 to 99% by weight, in particular from 75 to 97% by weight and specifically from 80 to 95% by weight, based on the total amount of glucose equivalents.

The aqueous medium M obtained in step iii) is used according to the invention in step iv) for the fermentative production of the desired organic compound. To this end, the medium M is subjected to a fermentation, where it is used for culturing the microorganisms employed in the fermentation. The respective organic compound is obtained in this process as a volatile or nonvolatile microbial metabolite.

As a rule, the dextrin-containing medium M will be cooled to the fermentation temperature, usually in the range of from 32 to 37° C., before supplying it to the fermentation.

If appropriate, the aqueous dextrin-containing medium M can be sterilized before the fermentation, where the microorganisms are, as a rule, destroyed by thermal or chemical methods. To this end, the aqueous medium M is usually heated at temperatures of above 80° C. The destruction, or lysis, of the cells can be accomplished immediately before the fermentation. To this end, all of the medium M is subjected to the lysis, or destruction, process. This can be accomplished for example thermally or chemically. However, it has proved to be unnecessary within the scope of the process according to the invention to carry out a sterilization step as described herein before the fermentation; rather, it has proved advantageous not to carry out such a sterilization step. Accordingly, a preferred embodiment of the invention relates to a process in which the medium M obtained in step iii) is supplied to the fermentation directly, i.e. without previously undergoing a sterilization process.

In the fermentation, the sugars present in the medium are metabolized. If the sugars present in the medium are present in the form of oligosaccharides, specifically in the form of dextrins, they are taken up by the microorganism either as such or after previously having been saccharified by saccharifying enzymes which have either been added or which are intrinsic to the strain, in particular glucoamylases, and metabolized. If no saccharifying enzymes are added and the sugars present in the medium are present in the form of oligosaccharides, specifically dextrins, the saccharification of the liquefied starch constituents is accomplished in parallel to the metabolization of the sugar, in particular of the monosaccharide glucose, by the microorganisms.

The fermentation can be carried out in the customary manner which is known to the skilled worker. To this end, the desired microorganism will, as a rule, be cultured in the liquid medium obtained by the method described herein.

The fermentation method can be carried out batchwise or else fed-batch-wise (including fed batch with intermediate harvests), the fed-batch process being preferred.

For example, the medium M obtained by the method according to the invention or a conventional sugar feedstock, i.e. metabolizable mono-, di- and/or oligosaccharides or media which comprise metabolizable mono-, di- and/or oligosaccharides, if appropriate after dilution with water and addition of customary media constituents such as buffers, nutrient salts, nitrogen feedstocks such as ammonium sulfate, urea and the like, complex nutrient media constituents, comprising amino acids such as yeast extracts, peptones, CSL and the like, and this microorganism can be multiplied under fermentation conditions until the microorganism concentration reaches the stationary state which is desired for the fermentation. Here, the sugar present in the fermentation medium is metabolized and the desired metabolite is formed (also known as batch process or batch phase).

When carrying out the fed-batch process, the medium M is added continuously or batchwise to the fermentation medium after the batch phase, for example when the total sugar concentration has dropped below a specific value.

A typical embodiment of the process according to the invention is the fed-batch process which comprises the following steps:

v) culturing the microorganism which is capable of overproducing the organic compound, in an aqueous fermentation medium F; and vi) addition of the medium M to the fermentation medium F in which the hydrolyzed starchy constituents present in the medium M, i.e. the sugars, are metabolized by the microorganisms which overproduce the organic compound, with generation of the organic compound.

In step v) it is possible, for example, first to adjust a conventional sugar-containing medium, as a rule a glucose solution, to a suitable sugar concentration by diluting it with an aqueous liquid, in particular water, and to add the media constituents which are conventionally used for the fermentation, such as buffers, nutrient salts, nitrogen sources such as ammonium sulfate, urea and the like, complex nutrient media constituents comprising amino acids such as yeast extracts, peptones, CSL and the like. Here, the ratio of sugar to liquid will, as a rule, preferably be chosen in such a way that the total concentration of monosaccharides in the fermentation medium F is less than 6% by weight, for example in the range of from >0 to 5% by weight, calculated as glucose equivalents and based on the total weight of the fermentation medium F. The sugar-containing batch medium thus prepared is inoculated with the desired microorganism and the microorganism is multiplied in the batch medium (fermentation medium F) under fermentation conditions until the microorganism concentration has reached a stationary state which is desired for the fermentation. Here, the sugar introduced into the fermentation medium F is metabolized, and the desired metabolite is formed.

The addition according to step vi) of the aqueous medium M to the fermentation medium F maintains the fermentation process, and the metabolite which is overproduced by the microorganism accumulates in the fermentation liquor. The volume ratio of medium M which is fed in to the batch medium (fermentation medium F) which was initially introduced and which comprises the microorganisms is generally in the range of from approximately 1:10 to 10:1 and preferably approximately 1:5 to 5:1 and specifically in the range of from 1:1 to 5:1. The sugar content in the fermentation liquor can be controlled in particular via the feed rate of the sugar-containing liquid medium. As a rule, the feed rate will be adjusted in such a way that the monosaccharide content in the fermentation liquor is within the range of from >0% by weight to approximately 5% by weight and in particular does not exceed a value of 3% by weight.

In a preferred embodiment, the fermentation medium F, in step v) (i.e. the batch medium in the present case) comprises essentially the medium M, the microorganisms which are capable of overproducing the organic compound, nutrient salts, conventional adjuvants such as bases or buffers and, if appropriate, water for dilution. To this end, the medium M will, if appropriate, be diluted to the desired sugar concentration, for example in the range of from 0.1 to 10% by weight, calculated as glucose equivalents and based on the total weight of the medium M, using it directly for making up the fermentation medium F (batch medium).

The sugar content of the dextrin-containing medium in accordance with step vi) employed for maintaining the fermentation is usually higher, for example in the abovementioned ranges, in order to minimize the dilution of the fermentation medium F.

Preferably, a procedure will be followed in which an aqueous medium M with a higher sugar concentration, for example at least 40% by weight, specifically at least 45% by weight and very specifically at least 50% by weight, calculated as glucose equivalents and based on the total weight of the aqueous medium M, is prepared. This medium M is then used firstly in accordance with step v) after dilution with water for making up the batch medium (fermentation medium F) and secondly in accordance with step vi) for addition to the fermentation medium F.

Naturally, in accordance with the invention, most of the sugar employed in the fermentation and to be metabolized, preferably at least 60% by weight, in particular at least 70% by weight, in the batch phase and/or in the fed-batch phase originates from the medium M. In one embodiment of the invention, part of the sugar, for example 1 to 50% by weight, in particular from 5 to 40% by weight and specifically 10 to 30% by weight, employed in the fermentation and to be metabolized originates from conventional sugar feedstocks. The conventional sugar feedstocks include mono- and disaccharides such as glucose and sucrose, but also media which comprise metabolizable mono-, di- and/or oligosaccharides in a concentration of at least 50% by weight and which are essentially free from solids which are insoluble in water, for example glucose syrups, sucrose syrups, thick juices, maltose syrups, dextrin syrups, but also waste products from the sugar production (molasses), in particular molasses from the beet sugar production, but also molasses from the cane sugar production.

The process according to the invention makes it possible to produce volatile and nonvolatile, in particular nonvolatile, microbial metabolites with at least 3 C atoms or with at least 2 C atoms and 1 N atom in a fermentative process.

In this context, nonvolatile products are understood as meaning those compounds which cannot be recovered by distillation from the fermentation liquor without undergoing decomposition. As a rule, these compounds have a boiling point above the boiling point of water, frequently above 150° C. and in particular above 200° C. under atmospheric pressure. As a rule, they are compounds which are in the solid state under standard conditions (298 K, 101.3 kPa).

However, it is also possible to employ the liquid medium M according to the invention in a fermentation for the production of nonvolatile microbial metabolites which, under atmospheric pressure, have a melting point below the boiling point of water and/or an oily consistency.

The term nonvolatile microbial metabolites comprises in particular organic mono-, di- and tricarboxylic acids which preferably have 3 to 10 carbon atoms and which, if appropriate, have one or more, for example 1, 2, 3 or 4, hydroxyl groups attached to them, for example tartaric acid, itaconic acid, succinic acid, propionic acid, lactic acid, 3-hydroxypropionic acid, fumaric acid, maleic acid, 2,5-furandicarboxylic acid, glutaric acid, levulic acid, gluconic acid, aconitic acid and diaminopimelic acid, citric acid; proteinogenic and non-proteinogenic amino acids, for example lysine, glutamate, methionine, phenylalanine, aspartic acid, tryptophan and threonine; purine and pyrimidine bases; nucleosides and nucleotides, for example nicotinamide adenine dinucleotide (NAD) and adenosine-5'-monophosphate (AMP); lipids; saturated and unsaturated fatty acids having preferably 10 to 22 carbon atoms, for example γ-linolenic acid, dihomo-γ-linolenic acid, arachidonic acid, eicosapentaenoic acid and docosahexaenoic acid; diols having preferably 3 to 8 carbon atoms, for example propanediol and butanediol; polyhydric alcohols (also referred to as alcohols with higher functionality) having 3 or more, for example 3, 4, 5 or 6, OH groups, for example glycerol, sorbitol, mannitol, xylitol and arabinitol; long-chain (also referred to as longer-chain) alcohols having at least 4 carbon atoms, for example 4 to 22 carbon atoms, for example butanol; carbohydrates, for example hyaluronic acid and trehalose; aromatic compounds, for example aromatic amines, vanillin and indigo; vitamins and provitamins, for example ascorbic acid, vitamin $B_6$, vitamin $B_{12}$ and riboflavin, cofactors and what are known as nutraceuticals; proteins, for example enzymes such as amylases, pectinases, acid, hybrid or neutral cellulases, esterases such as lipases, pancreases, proteases, xylanases and oxidoreductases such as laccase, catalase and peroxidase, glucanases, phytases; carotenoids, for example lycopene, β-carotene, astaxanthin, zeaxanthin and canthaxanthin; ketones having preferably 3 to 10 carbon atoms and, if appropriate, 1 or more hydroxyl groups, for example acetone and acetoin; lactones, for example γ-butyrolactone, cyclodextrins, biopolymers, for example polyhydroxyacetate, polyesters, for example polylactide, polysaccharides, polyisoprenoids, polyamides; and precursors and derivatives of the abovementioned compounds. Other compounds which are suitable as nonvolatile microbial metabolites are described by Gutcho in Chemicals by Fermentation, Noyes Data Corporation (1973), ISBN: 0818805086.

The term "cofactor" comprises nonproteinaceous compounds which are required for the occurrence of a normal enzyme activity. These compounds can be organic or inorganic; preferably, the cofactor molecules of the invention are organic. Examples of such molecules are NAD and nicotinamide adenine dinucleotide phosphate (NADP); the precursor of these cofactors is niacin.

The term "nutraceutical" comprises food additives which promote health in plants and animals, in particular humans. Examples of such molecules are vitamins, antioxidants and certain lipids, for example polyunsaturated fatty acids.

The metabolites produced are selected in particular among enzymes, amino acids, vitamins, disaccharides, aliphatic mono- and dicarboxylic acids having 3 to 10 C atoms, aliphatic hydroxycarboxylic acids having 3 to 10 C atoms, ketones having 3 to 10 C atoms, alkanols having 4 to 10 C atoms and alkanediols having 3 to 10 and in particular 3 to 8 C atoms.

It is clear to the skilled worker that the compounds thus produced fermentatively are obtained in each case in the enantiomeric form produced by the microorganisms employed (if different enantiomers exist). Thus, as a rule, the respective L-enantiomer is obtained in the case of amino acids.

The microorganisms employed in the fermentation depend in a manner known per se on the microbial metabolites in question, as specified in detail hereinbelow. They can be of natural origin or genetically modified. Examples of suitable microorganisms and fermentation processes are those given in Table A hereinbelow:

TABLE A

| Substances | Microorganism | Reference |
|---|---|---|
| Tartaric acid | Lactobacilli, (for example Lactobacillus delbrueckii) | Rehm, H. -J.: Biotechnology, Weinheim, VCH, 1980 and 1993-1995; Gutcho, Chemicals by Fermentation, Noyes Data Corporation (1973), |
| Itaconic acid | Aspergillus terreus, Aspergillus itaconicus | Jakubowska, in Smith and Pateman (Eds.), Genetics and Physiology of Aspergillus, London: Academic Press 1977; Miall, in Rose (Ed.), Economic Microbiology, Vol. 2, pp. 47-119, London: Academic Press 1978; U.S. Pat. No. 3,044,941 (1962). |
| Succinic acid | Actinobacillus sp. 130Z, Anaerobiospirillum succiniproducens, Actinobacillus succinogenes, E. coli | Int. J. Syst. Bacteriol. 26, 498-504 (1976); EP 249773 (1987), Inventors: Lemme and Datta; U.S. Pat. No. 5,504,004 (1996), Inventors: Guettler, Jain and Soni; Arch. Microbiol. 167, 332-342 (1997); Guettler MV, Rumler D, Jain MK., Actinobacillus succinogenes sp. nov., a novel succinic-acid-producing strain from the bovine rumen. Int J Syst Bacteriol. 1999 Jan; 49 Pt 1: 207-16; U.S. Pat. No. 5,723,322, U.S. Pat. No. 5,573,931, U.S. Pat. No. 5,521,075, WO 99/06532, U.S. Pat. No. 5,869,301, U.S. Pat. No. 5,770,435 |
| Hydroxypropionic acid | Lactobacillus delbrückii, L. leichmannii or Sporolactobacillus inulinus | RÖMPP Online Version 2.2 |
| Propionic acid | Propionibacterium, for example P. arabinosum, P. schermanii, P. freudenreichii, Clostridium propionicum, | Rehm, H. -J.: Biotechnology, Weinheim, VCH, 1980 and 1993-1995; Gutcho, Chemicals by Fermentation, Noyes Data Corporation (1973), |
| Diaminopimelic acid | Corynebacterium glutamicum | Rehm, H. -J.: Biotechnology, Weinheim, VCH, 1980 and 1993-1995; Gutcho, Chemicals by Fermentation, Noyes Data Corporation (1973), |
| Citric acid | Aspergillus niger, Aspergillus wentii | Crit. Rev. Biotechnol. 3, 331-373 (1986); Food Biotechnol. 7, 221-234 (1993); 10, 13-27 (1996). |
| Aconitic acid | Aspergillus niger, Aspergillus wentii | Crit. Rev. Biotechnol. 3, 331-373 (1986); Food Biotechnol. 7, 221-234 (1993); 10, 13-27 (1996).; Rehm, H. -J.: Biotechnology, Weinheim, VCH, 1980 and 1993-1995; |
| Malic acid | Aspergilli, for example Aspergillus flavus, A. niger, A. oryzae, Corynebacterium | U.S. Pat. No. 3,063,910 |

TABLE A-continued

| Substances | Microorganism | Reference |
| --- | --- | --- |
| Gluconic acid | *Aspergilli*, for example *A. niger* | Gutcho, Chemicals by Fermentation, Noyes Data Corporation (1973), |
| Butyric acid | *Clostridium* (for example *Clostridium acetobutylicum*, *C. butyricum*) | Rehm, H. -J.: Biotechnology, Weinheim, VCH, 1980 and 1993-1995; |
| Lactic acid | *Lactobacillus* for example *L. delbrückii*, *L. leichmannii*, | Rehm, H. -J.: Biotechnology, Weinheim, VCH, 1980 and 1993-1995; |
| Lysine | *Corynebacterium glutamicum* | Ikeda, M.: Amino Acid Production Process (2003), Adv. Biochem. Engin/Biotechnol 79, 1-35. |
| Glutamate | *Corynebacterium glutamicum* | Ikeda, M.: Amino Acid Production Process (2003), Adv. Biochem. Engin/Biotechnol 79, 1-35. |
| Methionine | *Corynebacterium glutamicum* | Ikeda, M.: Amino Acid Production Process (2003), Adv. Biochem. Engin/Biotechnol 79, 1-35. |
| Phenylalanine | *Corynebacterium glutamicum*, *E. coli* | Trends Biotechnol. 3, 64-68 (1985); J. Ferment. Bioeng. 70, 253-260 (1990). |
| Threonine | *E. coli* | Ikeda, M.: Amino Acid Production Process (2003), Adv. Biochem. Engin/Biotechnol 79, 1-35. |
| Aspartic acid | *E. coli* | Ikeda, M.: Amino Acid Production Process (2003), Adv. Biochem. Engin/Biotechnol 79, 1-35 and references cited therein, Gutcho, Chemicals by Fermentation, Noyes Data Corporation (1973) |
| Purine and pyrimidine bases | *Bacillus subtilis* | Rehm, H. -J.: Biotechnology, Weinheim, VCH, 1980 and 1993-1995; Gutcho, Chemicals by Fermentation, Noyes Data Corporation (1973), |
| Nicotinamide adenine dinucleotide (NAD) | *Bacillus subtilis* | Rehm, H. -J.: Biotechnology, Weinheim, VCH, 1980 and 1993-1995; Gutcho, Chemicals by Fermentation, Noyes Data Corporation (1973), |
| Adenosine-5'-monophosphate (AMP) | *Bacillus subtilis* | Rehm, H. -J.: Biotechnology, Weinheim, VCH, 1980 and 1993-1995; Gutcho, Chemicals by Fermentation, Noyes Data Corporation (1973), |
| γ-Linolenic acid | *Mucor*, *Mortiella*, *Aspergillus* spp. | Gill, I., Rao, V.: Polyunsaturated fatty acids, part 1: occurence, biological activities and applications (1997). Trends in Biotechnology 15 (10), 401-409; Zhu, H.: Utilization of Rice Brain by *Pythium irregulare* for Lipid Production. Master Thesis Lousiana State University, 31.10.2002 (URN etd-1111102-205855). |
| Dihomo-γ-linolenic acid | *Mortiella*, *Conidiobolus*, *Saprolegnia* spp. | Gill, I., Rao, V.: Polyunsaturated fatty acids, part 1: occurence, biological activities and applications (1997). Trends in Biotechnology 15 (10), 401-409; Zhu, H.: Utilization of Rice Brain by *Pythium irregulare* for Lipid Production. Master Thesis Lousiana State University, 31.10.2002 (URN etd-1111102-205855). |
| Arachidonic acid | *Mortiella*, *Phytium* spp. | Gill, I., Rao, V.: Polyunsaturated fatty acids, part 1: occurence, biological activities and applications (1997). Trends in Biotechnology 15 (10), 401-409; Zhu, H.: Utilization of Rice Brain by *Pythium irregulare* for Lipid Production. Master Thesis Lousiana State University, 31.10.2002 (URN etd-1111102-205855). |
| Eicosapentaenoic acid | *Mortiella*, *Phytium* spp., *Rhodopseudomonas*, *Shewanella* spp. | Gill, I., Rao, V.: Polyunsaturated fatty acids, part 1: occurence, biological activities and applications (1997). Trends in Biotechnology 15 (10), 401-409; Zhu, H.: Utilization of Rice Brain by *Pythium irregulare* for Lipid Production. Master Thesis Lousiana State University, 31.10.2002 (URN etd-1111102-205855). |
| Docosahexaenoic acid | *Thraustochytrium*, *Entomophthora* spp., *Rhodopseudomonas*, *Shewanella* spp. | Gill, I., Rao, V.: Polyunsaturated fatty acids, part 1: occurence, biological activities and applications (1997). Trends in Biotechnology 15 (10), 401-409; Zhu, H.: Utilization of Rice Brain by *Pythium irregulare* for Lipid Production. Master Thesis Lousiana State University, 31.10.2002 (URN etd-1111102-205855). |
| Propanediol | *E. coli* | DE 3924423, U.S. Pat. No. 440379, WO 9635799, U.S. Pat. No. 5,164,309 |
| Butanediol | *Enterobacter aerogenes*, *Bacillus subtilis*, *Klebsiella oxytoca* | Rehm, H. -J.: Biotechnology, Weinheim, VCH, 1980 and 1993-1995; Gutcho, Chemicals by Fermentation, Noyes Data Corporation (1973), H. G. SCHLEGEL and H. W. JANNASCH, 1981; Afschar et al.: Mikrobielle Produktion von 2,3-Butandiol [Microbial production of 2,3-butane diol. CIT 64 (6), 2004, 570-571 |

TABLE A-continued

| Substances | Microorganism | Reference |
|---|---|---|
| Butanol | *Clostridium* (e.g. *Clostridium acetobutylicum*, *C. propionicum*) | Rehm, H. -J.: Biotechnology, Weinheim, VCH, 1980 and 1993-1995; Gutcho, Chemicals by Fermentation, Noyes Data Corporation (1973), |
| Glycerol | Yeast, *Saccharomyces rouxii* | Gutcho, Chemicals by Fermentation, Noyes Data Corporation (1973), |
| Mannitol | *Aspergillus candida*, *Torulopsis mannitofaciens* | Gutcho, Chemicals by Fermentation, Noyes Data Corporation (1973), |
| Arabitol | *Saccharomyces rouxii*, *S. mellis*, *Sclerotium glucanicum*, *Pichia ohmeri* | Gutcho, Chemicals by Fermentation, Noyes Data Corporation (1973), |
| Xylitol | *Saccharomyces cerevisiae* | Gutcho, Chemicals by Fermentation, Noyes Data Corporation (1973), |
| Hyaluronic acid | *Streptococcus* spp. | Rehm, H. -J.: Biotechnology, Weinheim, VCH, 1980 and 1993-1995; |
| Trehalose | *Brevibacterium*, *Corynebacterium*, *Microbacterium*, *Arthrobacter* spp., *Pleurotus* genus, *Filobasidium floriforme* | JP 05099974, JP 06311891, FR 2671099, EP 0555540, JP 3053791, Miyazaki, J. -I., Miyagawa, K. -I., Sugiyama, Y.: Trehalose Accumulation by Basidiomycotinous Yeast, Filobasidium floriforme. Journal of Fermentation and Bioengineering 81, (1996) 4, 315-319. |
| Ascorbic acid | *Gluconobacter melanogenes* | RÖMPP Online Version 2.2 |
| Vitamin $B_{12}$ | *Propionibacterium* spp., *Pseudomonas denitrificans* | Chem. Ber. 1994, 923-927; RÖMPP Online Version 2.2 |
| Riboflavin | *Bacillus subtilis*, *Ashbya gossypii* | WO 01/011052, DE 19840709, WO 98/29539, EP 1186664; Fujioka, K.: New biotechnology for riboflavin (vitamin B2) and character of this riboflavin. Fragrance Journal (2003), 31(3), 44-48. |
| Vitamin $B_6$ | *Rhizobium tropici*, *R. meliloti* | EP0765939 |
| Enzymes | *Aspergilli* (for example *Aspergillus niger A. oryzae*), *Trichoderma*, *E. coli*, *Hansenula* or *Pichia* (for example *Pichia pastorius*), *Bacillus* (for example *Bacillus licheniformis B. subtilis*) and many others | Rehm, H. -J.: Biotechnology, Weinheim, VCH, 1980 and 1993-1995; Gutcho, Chemicals by Fermentation, Noyes Data Corporation (1973), |
| Zeaxanthin | *Dunaliella salina* | Jin et al (2003) Biotech. Bioeng. 81: 115-124 |
| Canthaxanthin | *Brevibacterium* | Nelis et al (1991) J Appl Bacteriol 70: 181-191 |
| Lycopene | *Blakeslea trispora*, *Candida utilis* | WO 03/056028, EP 01/201762, WO 01/12832, WO 00/77234, Miura et al (1998) Appl Environ Microbiol 64: 1226-1229 |
| β-Carotene | *Blakeslea trispora*, *Candida utilis* | Kim S., Seo W., Park Y., Enhanced production of beta-carotene from *Blakeslea trispora* with Span 20, Biotechnology Letters, Vol 19, No 6, 1997, 561-562; Mantouridou F., Roukas T.: Effect of the aeration rate and agitation speed on beta-carotene production and morphology of *Blakeslea trispora* in a stirred tank reactor: mathematical modelling, Biochemical Engineering Journal 10 (2002), 123-135; WO 93/20183; WO 98/03480, Miura et al (1998) Appl Environ Microbiol 64: 1226-1229 |
| Astaxanthin | *Phaffia rhodozyma*; *Candida utilis* | U.S. Pat. No. 5,599,711; WO 91/02060, Miura et al (1998) Appl Environ Microbiol 64: 1226-1229 |
| Polyhydroxy-alkanoates, polyesters | *Escherchia coli*, *Alcaligenes latus*, and many others | S. Y. Lee, Plastic Bacteria Progress and Prospects for polyhydroxyalkanoate production in bacteria, Tibtech, Vol. 14, (1996), pp. 431-438., Steinbüchel, 2003; Steinbüchel (Ed.), Biopolymers, 1st ed., 2003, Wiley-VCH, Weinheim and references cited therein |
| Polysaccharides | *Leuconostoc mesenteroides*, *L. dextranicum*, *Xanthomonas campestris*, and many others | Rehm, H. -J.: Biotechnology, Weinheim, VCH, 1980 and 1993-1995; Gutcho, Chemicals by Fermentation, Noyes Data Corporation (1973), |

TABLE A-continued

| Substances | Microorganism | Reference |
|---|---|---|
| Polyisoprenoids | *Lactarius* sp., *Hygrophorus* sp., *Russula* sp. | Steinbüchel (Ed.), Biopolymers, 1st ed., 2003, Wiley-VCH, Weinheim and references cited therein |
| Acetone | *Clostridium* (for example *Clostridium acetobutylicum*, *C. propionicum*) | Rehm, H. -J.: Biotechnology, Weinheim, VCH, 1980 and 1993-1995; Gutcho, Chemicals by Fermentation, Noyes Data Corporation (1973), |
| Acetoin | *Enterobacter aerogenes*, *Clostridium acetobutylicum*, *Lactococcus lactis* | Lengeler, J. W., Drews, G., Schlegel, H. G.: Eds., Biology of the Procaryotes, Thieme, Stuttgart (1999), p. 307; RÖMPP Online-Edition |
| Vanillin | *Pseudomonas putida*, *Amycolatopsis* sp. | Priefert, H., Rabenhorst, J., Seinbüchel, A. Biotechnological production of vanillin. Appl. Microbiol. Biotechnol. 56, 296-314 (2001) |
| Thuringensin | *Bacillus thuringiensis* | Jian-Zhong Jong et al.: Fed-batch culture of *Bacillus thuringiensis* for thuringensin production in a tower type bioreactor. Biotechnology and Bioengineering 48 (3) (2004), 207-213. |
| Polyketides | *Streptomyces fradiae*, *Sorangium cellulosum* | Kirst: Fermentation-derived compounds as a source for new products. Pure & Appl. Chem. 70 (2), (1998), 335-338; Zirkle et al.: Heterologous production of the antifungal polyketide antibiotic soraphen A of Sorangium cellulosum So ce26 in *Streptomyces lividans*. Microbiology 150 (8), (2004), 2761-74. |
| Gibberellic acid | *Gibberella fujikuroi* | Hollmann et al.: Extractive fermentation of Gibberellic acid using Gibberella fujikuroi. CIT 7 (1995), 892-895. |
| Indigo | *Escherichia coli* JB 102 | Berry, A., Dodge, T. C., Pepsin, M., Weyler, W.: Application of metabolic engineering to improve both the production and use of biotech indigo. Journal of Industrial Microbiology & Biotechnology 28 (2002), 127-133. |

In preferred embodiments of the invention, the organic compound which has been produced is selected among mono-, di- and tricarboxylic acids which optionally have hydroxyl groups attached to them and which have 3 to 10 C atoms, among proteinogenic and nonproteinogenic amino acids, purine bases, pyrimidine bases; nucleosides, nucleotides, lipids; saturated and unsaturated fatty acids; diols having 4 to 10 C atoms, polyhydric alcohols having 3 or more hydroxyl groups, longer-chain alcohols having at least 4 C atoms, carbohydrates, aromatic compounds, vitamins, provitamins, cofactors, nutraceuticals, proteins, carotenoids, ketones having 3 to 10 C atoms, lactones, biopolymers and cyclodextrins.

A first preferred embodiment of the invention relates to the use of a sugar-comprising liquid medium which can be obtained in accordance with the invention in a fermentative production of enzymes such as phytases, xylanases or glucanases.

A second preferred embodiment of the invention relates to the use of a sugar-comprising liquid medium which can be obtained in accordance with the invention in a fermentative production of amino acids such as lysine, methionine, threonine and glutamate.

A further preferred embodiment of the invention relates to the use of a sugar-comprising liquid medium which can be obtained in accordance with the invention in a fermentative production of vitamins such as pantothenic acid and riboflavin, and the precursors and derivatives.

Further preferred embodiments of the invention relate to the use of a sugar-comprising liquid medium which can be obtained in accordance with the invention in a fermentative production of mono-, di- and tricarboxylic acids, in particular aliphatic mono- and dicarboxylic acids having 3 to 10 C atoms, such as propionic acid, fumaric acid and succinic acid;

aliphatic hydroxycarboxylic acids having 3 to 10 C atoms, such as lactic acid;

longer-chain alkanols as mentioned above, in particular alkanols having 4 to 10 C atoms, such as butanol;

diols as mentioned above, in particular alkanediols having 3 to 10, in particular 3 to 8, C atoms, such as propanediol;

ketones as mentioned above, in particular ketones having 3 to 10 C atoms, such as acetone; and carbohydrates as mentioned above, in particular disaccharides such as trehalose.

In a further especially preferred embodiment, the metabolite produced by the microorganisms in the fermentation are polyhydroxyalkanoates such as poly-3-hydroxybutyrate and copolyesters with other organic hydroxycarboxylic acids such as 3-hydroxyvaleric acid, 4-hydroxybutyric acid and others which are described in Steinbüchel (loc. cit.), including for example long-chain (also referred to as longer-chain) hydroxycarboxylic acids such as 3-hydroxyoctanoic acid, 3-hydroxydecanoic acid and 3-hydroxytetradecanoic acid, and mixtures of these. To carry out the fermentation, analogous conditions and procedures as have been described for other carbon feedstocks, for example in S. Y. Lee, Plastic Bacteria Progress and prospects for polyhydroxyalkanoate production in bacteria, Tibtech, Vol. 14, (1996), pp. 431-438, may be employed.

In a preferred embodiment, the microorganisms which are employed in the fermentation are therefore selected among natural or recombinant microorganisms which overproduce at least one of the following metabolites:

enzymes such as phytase, xylanase or glucanase;

amino acids such as lysine, threonine or methionine;

vitamins such as pantothenic acid and riboflavin; and their precursors and/or derivatives;

disaccharides such as trehalose;

aliphatic mono- and dicarboxylic acids having 3 to 10 C atoms, such as propionic acid, fumaric acid and succinic acid;
aliphatic hydroxycarboxylic acids having 3 to 10 C atoms such as lactic acid;
polyhydroxyalkanoates such as poly-3-hydroxybutyrate and copolyesters of 3-hydroxybutyric acid;
ketones having 3 to 10 C atoms such as acetone;
alkanols having 4 to 10 C atoms such as butanol; and alkanediols having 3 to 8 C atoms such as propanediol.

Suitable microorganisms are usually selected among the genera *Corynebacterium, Bacillus, Ashbya, Escherichia, Aspergillus, Alcaligenes, Actinobacillus, Anaerobiospirillum, Lactobacillus, Propionibacterium, Rhizopus* and *Clostridium*, in particular among strains of *Corynebacterium glutamicum, Bacillus subtilis, Ashbya gossypii, Escherichia coli, Aspergillus niger* or *Alcaligenes latus, Anaerobiospirillum succiniproducens, Actinobacillus succinogenes, Lactobacillus delbruckii, Lactobacillus leichmannii, Propionibacterium arabinosum, Propionibacterium schermanii, Propionibacterium freudenreichii, Clostridium propionicum, Clostridium formicoaceticum, Clostridium acetobutylicum, Rhizopus arrhizus* and *Rhizopus oryzae*.

In a preferred embodiment, the microorganism employed in the fermentation is a strain of the genus *Corynebacterium*, in particular a strain of *Corynebacterium glutamicum*. In particular, it is a strain of the genus *Corynebacterium*, specifically of *Corynebacterium glutamicum*, which overproduces an amino acid, specifically lysine, methionine or glutamate.

In a further preferred embodiment, the microorganism employed in the fermentation is a strain of the genus *Escherichia*, in particular a strain of *Escherichia coli*. In particular, it is a strain of the genus *Escherichia*, specifically of *Escherichia coli*, which overproduces an amino acid, specifically lysine, methionine or threonine.

In a specific preferred embodiment, the metabolite produced by the microorganisms in the fermentation is lysine. To carry out the fermentation, analogous conditions and procedures as have been described for other carbon feedstocks, for example in Pfefferle et al., loc. cit. and U.S. Pat. No. 3,708,395, can be employed. In principle, both a continuous and a discontinuous (batch or fed-batch) mode of operation are suitable, with the fed-batch mode being preferred.

In a further especially preferred embodiment, the metabolite produced by the microorganisms in the fermentation is methionine. To carry out the fermentation, analogous conditions and procedures as have been described for other carbon feedstocks, for example in WO 03/087386 and WO 03/100072, may be employed.

In a further especially preferred embodiment, the metabolite produced by the microorganisms in the fermentation is pantothenic acid. To carry out the fermentation, analogous conditions and procedures as have been described for other carbon feedstocks, for example in WO 01/021772, may be employed.

In a further especially preferred embodiment, the metabolite produced by the microorganisms in the fermentation is riboflavin. To carry out the fermentation, analogous conditions and procedures as have been described for other carbon feedstocks, for example in WO 01/011052, DE 19840709, WO 98/29539, EP 1 186 664 and Fujioka, K.: New biotechnology for riboflavin (vitamin B2) and character of this riboflavin. Fragrance Journal (2003), 31(3), 44-48, may be employed.

In a further especially preferred embodiment, the metabolite produced by the microorganisms in the fermentation is fumaric acid. To carry out the fermentation, analogous conditions and procedures as have been described for other carbon feedstocks, for example in Rhodes et al, Production of Fumaric Acid in 20-L Fermentors, Applied Microbiology, 1962, 10 (1), 9-15, may be employed.

In a further especially preferred embodiment, the metabolite produced by the microorganisms in the fermentation is succinic acid. To carry out the fermentation, analogous conditions and procedures as have been described for other carbon feedstocks, for example in Int. J. Syst. Bacteriol. 26, 498-504 (1976); EP 249773 (1987), to Lemme and Datta; U.S. Pat. No. 5,504,004 (1996), to Guettler, Jain and Soni; Arch. Microbiol. 167, 332-342 (1997); Guettler M V, Rumler D, Jain M K., *Actinobacillus succinogenes* sp. nov., a novel succinic-acid-producing strain from the bovine rumen. Int J Syst Bacteriol. 1999 January; 49 Pt 1:207-16; U.S. Pat. No. 5,723,322, U.S. Pat. No. 5,573,931, U.S. Pat. No. 5,521,075, WO 99/06532, U.S. Pat. No. 5,869,301 or U.S. Pat. No. 5,770,435, may be employed.

In a further especially preferred embodiment, the metabolite produced by the microorganisms in the fermentation is a phytase. To carry out the fermentation, analogous conditions and procedures as have been described for other carbon feedstocks, for example in WO 98/55599, may be employed.

The fermentation generates a fermentation liquor which, in addition to the desired microbial metabolite, essentially comprises the biomass produced during the fermentation, the nonmetabolized constituents of the liquefied starch solution and, in particular, the nonstarchy solid constituents of the starch feedstock such as, for example, fibers and nonutilized sugars, and also nonutilized buffer and nutrient salts. In the present application, this liquid medium is also referred to as fermentation liquor, the fermentation liquor also comprising the dextrin-containing medium (I) in which the sugars present have only been subjected to partial or incomplete fermentative conversion, i.e. in which a partial or incomplete microbial metabolization of the utilizable sugars (for example mono- and disaccharides) has taken place.

Before the isolation or depletion of a microbial metabolite or before the removal of the volatile constituents of the fermentation liquor, a sterilization step is, if appropriate, carried out in the above-described manner.

A specific embodiment (I) of the invention relates to a process in which at least one microbial metabolite is depleted or isolated from the fermentation liquor. Most of the volatile constituents of the fermentation liquor are subsequently removed, giving rise to a solid or semisolid protein composition. A more detailed description for carrying out such a process, and of the protein composition obtained, is subject matter of WO 2005/116228 (PCT/EP2005/005728) of the applicant company, which is referred to with regard to further details.

The isolation or depletion of the metabolites from the fermentation liquor, i.e. the organic compound having at least 3 C atoms or having at least 2 C atoms and at least one N atom (hereinbelow also referred to as product of value) is usually carried out in such a way that at least one metabolite is depleted or isolated from the fermentation liquor so that the content of this metabolite in the fermentation liquor which remains amounts to not more than 20% by weight, in particular not more than 10% by weight, specifically not more than 5% by weight and very specifically not more than 2.5% by weight, in each case based on the total weight of the remaining fermentation liquor.

The microbial metabolite can be isolated or depleted from the fermentation liquor in one or more steps. An essential step in this context is the removal of the solid constituents from the fermentation liquor. This can be carried out either before or after isolation of the product of value. Methods conventionally used in the art which also comprise steps for the rough cleaning and the fine purification of the products of value and for formulation are known both for the isolation of products of value and for the removal of solids, i.e. solid-liquid phase separation (for example described in Belter, P. A, Bioseparations: Downstream Processing for Biotechnology, John Wiley & Sons (1988), and Ullmann's Encyclopedia of Industrial Chemistry, 5th ed. on CD-ROM, Wiley-VCH).

To isolate the product of value, a procedure can advantageously be followed in which the solid constituents are first removed from the fermentation liquor, for example by means of centrifugation or filtration, and the product of value is subsequently isolated from the liquid phase, for example by crystallization, precipitation, adsorption or distillation. As an alternative, the product of value can also be isolated directly from the fermentation liquor, for example by using chromatographic methods or extractive methods. A chromatographic method which must be mentioned in particular is ion-exchange chromatography, where the product of value can be isolated selectively on the chromatography column. In this case, the removal of the solids from the fermentation liquor which remains is advantageously carried out for example by decanting, evaporation and/or drying.

In the case of volatile or oily compounds, it is, as a rule, necessary to monitor the maximum temperatures during processing, in particular during drying. These compounds can advantageously also be prepared by formulating them in pseudo-solid form on adsorbents. Adsorbents which are suitable for this purpose are detailed for example in WO 2005/116228 (PCT/EP2005/005728) of the applicant company. Examples of compounds which can advantageously be prepared in this manner are γ-linolenic acid, dihomo-γ-linolenic acid, arachidonic acid, eicosapentaenoic acid and docosahexaenoic acid, furthermore propionic acid, lactic acid, propanediol, butanol and acetone. These compounds in pseudo-solid formulation are also understood as being, for the purposes of the present invention, nonvolatile microbial metabolites in solid form.

A further specific embodiment (II) relates to a process in which the volatile constituents of the fermentation liquor are substantially removed, without previously isolating or depleting a nonvolatile microbial metabolite, and, if appropriate, without previously removing at least some solid constituents, giving rise to a solid formulation of a nonvolatile microbial metabolite. A more detailed description for carrying out such a process can be found in PCT/EP2006/066057 (earlier patent application DE 10 2005 042 541.0) of the applicant company.

"Substantially" means that, once the volatile constituents have been removed, a solid or at least semisolid residue remains which can, if appropriate, be converted into solid product by addition of solids. As a rule, this means the removal of the volatile constituents down to a residual moisture content of not more than 30% by weight, frequently not more than 20% by weight and in particular not more than 15% by weight. As a rule, the volatile constituents of the fermentation liquor will advantageously be removed from the fermentation liquor down to a residual moisture content in the range of from 0.2 to 30% by weight, preferably 1 to 20% by weight, especially preferably 2 to 15% by weight and very especially preferably 5 to 15% by weight, based on the total weight of the solid constituents determined after drying. The residual moisture content can be determined by conventional methods with which the skilled worker is familiar, for example by means of thermogravimetry (Hemminger et al., Methoden der thermischen Analyse [Methods of thermal analysis], Springer Verlag, Berlin, Heidelberg, 1989).

Obtaining the nonvolatile metabolite(s) in solid form from the fermentation liquor can be effected in one, two or more steps, in particular in one- or two-step procedures. As a rule, at least one step, in particular the final step, for obtaining the metabolite in solid form will comprise a drying step.

In the one-step procedure, the volatile constituents of the fermentation liquor will be removed, if appropriate after aforementioned preliminary removal, until the desired residual moisture content is reached.

In the two- or multi-step procedure, the fermentation liquor will first be concentrated, for example by filtration (microfiltration, ultrafiltration) or thermally by evaporating a part of the volatile constituents. The amount of volatile constituents which are removed in this step amounts, as a rule, to 10 to 80% by weight and in particular 20 to 70% by weight, based on the dry matter of the volatile constituents of the fermentation liquor. In one or more subsequent steps, the remaining volatile constituents of the fermentation liquor are removed until the desired residual moisture content has been reached.

In accordance with this embodiment (II), the volatile constituents are essentially removed from the liquid medium without previous depletion or indeed isolation of the product of value. As a consequence, when removing the volatile constituents of the fermentation liquor, the nonvolatile metabolite is essentially not removed together with the volatile constituents of the liquid medium, but remains in the resulting residue together with at least a part, usually with most and in particular with all of the other solid constituents from the fermentation liquor. Accordingly, however, it is also possible to remove—preferably small—amounts of the desired nonvolatile microbial metabolite, as a rule not more than 20% by weight, for example 0.1 to 20% by weight, preferably not more than 10, in particular not more than 5% by weight, especially preferably not more than 2.5% by weight and very especially preferably not more than 1% by weight, based on the total dry matter of the metabolite, together with the volatile constituents of the fermentation liquor when removing these constituents. In a very especially preferred embodiment, the desired nonvolatile microbial metabolite remains to at least 90% by weight, in particular at least 95% by weight, specifically 99% by weight and very specifically approximately 100% by weight, in each case based on the total dry weight of the metabolite, as solid in mixture with the portion of the solid constituents of the fermentation medium which has been obtained after removal of the volatile constituents, or with all of the solid constituents of the fermentation medium.

If desired, a portion, for example 5 to 80% by weight and in particular 30 to 70% by weight, of the nonstarchy solid constituents can be separated from the fermentation liquor, for example by means of centrifugation or filtration, before the volatile constituents are removed. If appropriate, such a preliminary separation will be carried out in order to remove coarser solids particles which comprise no, or only small amounts of, nonvolatile microbial metabolite. This preliminary filtering can be carried out using conventional methods which are known to the skilled worker, for example using coarse sieves, nets, perforated orifice plates or the like. If appropriate, coarse solids particles may also be separated off in a centrifugal-force separator. The equipment employed here, such as decanter, centrifuges, sedicanter and separators are also known to the skilled worker. In this manner, a solid or semisolid, for example pasty, residue is obtained which comprises the nonvolatile metabolite and the nonvolatile, generally solid, nonstarchy constituents of the starch feedstock or at least large portions thereof, frequently at least 90% by weight or all of the solid nonstarchy constituents.

The properties of the dry metabolite, which is present together with the solid constituents of the fermentation, can be formulated in a manner known per se specifically with regard to a variety of parameters such as active substance content, particle size, particle shape, tendency to dust, hygroscopicity, stability, in particular storage stability, color, odor, flowing behavior, tendency to agglomerate, electrostatic charge, sensitivity to light and temperature sensitivity, mechanical stability and redispersibility, by addition of formulation auxiliaries such as carrier and coating materials, binders and other additives.

The formulation auxiliaries which are conventionally used include, for example, binders, carrier materials, powdering/flow adjuvants, furthermore color pigments, biocides, dispersants, antifoams, viscosity regulators, acids, alkalis, antioxidants, enzyme stabilizers, enzyme inhibitors, adsorbates, fats, fatty acids, oils or mixtures of these. Such formulation auxiliaries are advantageously employed as drying aids in particular when using formulation and drying methods such as spray drying, fluidized-bed drying and freeze-drying. Further details can be found in PCT/EP2006/066057 (earlier application DE 10 2005 042 541.0).

The amount of the abovementioned additives and, if appropriate, further additives such as coating materials can vary greatly, depending on the specific requirements of the metabolite in question and on the properties of the additives employed and can be for example in the range of from 0.1 to 80% by weight and in particular in the range of from 1 to 30% by weight, in each case based on the total weight of the product or substance mixture in its finished formulated form.

The addition of formulation auxiliaries can be effected before, during or after working up the fermentation liquor (also referred to as product formulation or solids design), in particular during drying. An addition of formulation auxiliaries before working up the fermentation liquor or the metabolite can be advantageous in particular for improving the processibility of the substances or products to be worked up. The formulation auxiliaries can be added either to the metabolite obtained in solid form or else to a solution or suspension comprising the metabolite, for example directly to the fermentation liquor after the fermentation has been completed or to a solution or suspension obtained during work-up and before the final drying step.

Thus, for example, the auxiliaries can be admixed with the suspension of the microbial metabolite; such a suspension can also be applied to a carrier material, for example by spraying on or mixing in. The addition of formulation auxiliaries during drying can be of importance for example when a solution or suspension comprising the metabolite is being sprayed. An addition of formulation auxiliaries is effected in particular after drying, for example when applying coatings/coating layers to dried particles. Further adjuvants can be added to the product both after drying and after an optional coating step.

Removing the volatile constituents from the fermentation liquor is effected in a manner known per se by customary methods for separating solid phases from liquid phases, including filtration methods and methods of evaporating volatile constituents of the liquid phases. Such methods, which may also comprise steps for roughly cleaning the products of value and formulation steps, are described, for example in Belter, P. A, Bioseparations: Downstream Processing for Biotechnology, John Wiley & Sons (1988), and Ullmann's Encyclopedia of Industrial Chemistry, 5th ed. on CD-ROM, Wiley-VCH. Methods, equipment, auxiliaries and general or specific embodiments which are known to the skilled worker which can be employed within the scope of product formulation or work up after the fermentation has ended are furthermore described in EP 1038 527, EP 0648 076, EP 835613, EP 0219 276, EP 0394 022, EP 0547 422, EP 1088 486, WO 98/55599, EP 0758 018 and WO 92/12645.

In a first variant of this embodiment (II), the nonvolatile microbial metabolite, if present in dissolved form in the liquid phase, will be converted from the liquid phase into the solid phase, for example by crystallization or precipitation. Thereafter, the nonvolatile solid constituents, including the metabolite, are separated, for example by means of centrifugation, decanting or filtration. Oily metabolites may also be separated off in a similar manner, the oily fermentation products in question being converted into a solid form by addition of adsorbents, for example silica, silica gels, loam, clay and active charcoal.

In a second variant of this embodiment (II), the volatile constituents are removed by evaporation. The evaporation can be effected in a manner known per se. Examples of suitable methods for evaporating volatile constituents are spray drying, fluidized-bed drying or fluidized-bed agglomeration, freeze drying, pneumatic driers and contact driers, and extrusion drying. A combination of the abovementioned methods with shape-imparting methods such as extrusion, pelleting or prilling may also be carried out. In these last-mentioned methods, it is preferred to employ partially or largely pre-dried metabolite-comprising substance mixtures.

In a preferred embodiment, the removal of the volatile constituents of the fermentation liquor comprises a spray-drying method or a fluidized-bed drying method, including fluidized-bed granulation. To this end, the fermentation liquor, if appropriate after a preliminary separation for removing coarse solids particles which comprise only small amounts of nonvolatile microbial metabolite, if any, is fed to one or more spray-drying or fluidized-bed-drying apparatuses. The transport, or feeding, of the solids-loaded fermentation liquor is expediently effected by means of customary transport devices for solid-comprising liquids, for example pumps, such as eccentric single-rotor screw pumps (for example from Delasco PCM) or high-pressure pumps (for example from LEWA Herbert Ott GmbH).

A fermentation using the sugar-containing liquid medium according to the invention can also be carried out in such a way that vii) a portion of not more than 50% by weight, for example in the range of from 5 to 45% by weight, based on the total weight, is removed from the medium M obtained in step iii) which comprises the nonstarchy solid constituents of the starch feedstock, and the remainder is supplied to a fermentation for the production of a first metabolite (A), for example a nonvolatile metabolite (A) in solid form or a volatile metabolite (A); and viii) this portion, if appropriate after previously having removed all or some of the nonstarchy solid constituents of the starch feedstock, is supplied to a fermentation for the production of a second metabolite (B), which is identical to, or different from, the metabolite (A).

If the nonstarchy solid constituents of (vii) are separated, the solids content of the remaining portion of the medium M amounts to preferably not more than 50% by weight, particularly not more than 30% by weight, especially preferably not more than 10% by weight and very especially preferably not more than 5% by weight. In such a case, it is particularly preferred to separate all of the solid before the fermentation for the production of the second metabolite (B).

This procedure makes possible, in the separate fermentation of vii), the use of microorganisms for which certain minimum requirements, for example with regard to the oxygen transfer rate, must be met. Suitable microorganisms which are employed in the separate fermentation of vii) are, for example, Bacillus species, preferably Bacillus subtilis. The compounds produced by such microorganisms in the separate fermentation are selected in particular from vitamins, cofactors and nutraceuticals, purine and pyrimidine bases, nucleosides and nucleotides, lipids, saturated and unsaturated fatty acids, aromatic compounds, proteins, carotenoids, specifically from vitamins, cofactors and nutraceuticals, proteins and carotenoids, and very specifically from riboflavin and calcium pantothenate.

A preferred embodiment of this procedure relates to parallel production of identical metabolites (A) and (B) in two separate fermentations. This is advantageous in particular in a case where different applications of the same metabolite have different purity requirements. Accordingly, the first metabolite (A), for example an amino acid to be used as feed additive, for example lysine, methionine, threonine, or glutamate is produced using the solids-containing fermentation liquor and the same second metabolite (B), for example the same amino acid to be used as food additive, is produced using the solids-depleted fermentation liquor of viii). Owing to the complete or partial removal of the non-starchy solid constituents, the complexity of the purification when working up the metabolite whose field of application has a higher purity requirement, for example as food additive, can be reduced.

In a further preferred embodiment, this procedure can be carried out for example as follows. A preferably large-volume fermentation for the production of metabolites A, for example amino acids such as lysine, methionine, glutamate or threonine, of citric acid or of ethanol, is implemented, for example in accordance with the processes described in WO 2005/116228 (PCT/EP2005/005728) or PCT/EP2006/066057 (earlier application DE 10 2005 042 541.0), or in accordance with the known processes for the fermentative production of bioethanol. In accordance with vii), some of the medium M obtained in step iii) is removed. The portion removed in accordance with vii) can be freed in accordance with viii) completely or in part from the solids by customary methods, for example centrifugation or filtration, depending on what is required in the fermentation for the production of B. The medium M obtained in this way, which is optionally fully or partially freed from the solids, is, in accordance with viii), fed to a fermentation for the production of a metabolite B. A solids stream separated in accordance with viii) is advantageously returned to the stream of the medium M of the large-volume fermentation.

If the microbial metabolite (A) which is produced in the large-volume fermentation is ethanol, the medium M produced in step iii) has concentrations of mono-, di- or oligosaccharides as are usual in the fermentative production of ethanol (bioethanol), for example in the range of from 25 to 33% by weight. Here, too, the separation of solids in accordance with step viii) is carried out in accordance with the fermentation requirements for producing the respective metabolite B.

In a preferred embodiment of the abovedescribed procedure, the metabolite B produced by the microorganisms in the fermentation is riboflavin. To carry out the fermentation, analogous conditions and procedures as have been described for other carbon feedstocks, for example in WO 01/011052, DE 19840709, WO 98/29539, EP 1186664 and Fujioka, K.: New biotechnology for riboflavin (vitamin B2) and character of this riboflavin. Fragrance Journal (2003), 31(3), 44-48, can be employed.

To carry out this variant of the process, a preferably large-volume fermentation is implemented for the production of metabolites A, for example of amino acids such as lysine, methionine or glutamate, of citric acid or of ethanol, as described above. In accordance with vii), some of the medium M obtained in step iii) is removed and freed in accordance with viii) completely or in part from the solids by customary methods, for example centrifugation or filtration. The medium M obtained therefrom, which is essentially fully or partially freed from the solids, is, in accordance with viii), fed to a fermentation for the production of metabolite B, in this case riboflavin. The solids stream separated in accordance with viii) is advantageously returned to the stream of the medium M of the large-volume fermentation.

The riboflavin-containing fermentation liquor which is thus generated in accordance with viii) can be worked up by analogous conditions and procedures as have been described for other carbon feedstocks, for example in DE 4037441, EP 464582, EP 438767 and DE 3819745. Following lysis of the cell mass, the riboflavin, which is present in crystalline form, is separated, preferably by decanting. Other ways of separating solids, for example filtration, are also possible. Thereafter, the riboflavin is dried, preferably by means of spray dryers and fluidized-bed dryers. As an alternative, the riboflavin-containing fermentation mixture produced in accordance with viii) can be processed under analogous conditions and using analogous procedures as described in, for example, EP 1048668 and EP 730034. After pasteurization, the fermentation liquor is centrifuged, and the remaining solids-containing fraction is treated with a mineral acid. The riboflavin formed is removed from the aqueous-acidic medium by filtration, washed, if appropriate, and subsequently dried.

In a further preferred embodiment of this procedure, the metabolite B produced by the microorganisms in the fermentation is pantothenic acid. To carry out the fermentation, analogous conditions and procedures as have been described for other carbon feedstocks, for example in WO 01/021772, can be employed.

To carry out this process variant, a procedure such as described above for riboflavin may be followed. The medium M which has been subjected to a preliminary purification in accordance with viii) and which has preferably been essentially freed from the solids, is fed to a fermentation in accordance with viii) for the production of pantothenic acid. Here, the fact that the viscosity is reduced in comparison with the solids-containing liquid medium is particularly advantageous. The separated solids stream is preferably returned to the stream of the sugar-containing liquid medium of the large-volume fermentation.

The pantothenic-acid-containing fermentation liquor produced in accordance with viii) can be worked up under analogous conditions and using analogous procedures as have been described for other carbon feedstocks, for example in EP 1 050 219 and WO 01/83799. After all of the fermentation liquor has been pasteurized, the remaining solids are separated, for example by centrifugation or filtration. The clear runoff obtained in the solids separation step is partly evaporated, if appropriate treated with calcium chloride and dried, in particular spray dried.

The solids which have been separated off can be obtained together with the respective desired microbial metabolite (A) within the scope of the parallel large-volume fermentation process.

After the drying and/or formulation step, whole or milled cereal kernels preferably maize, wheat, barley, millet, triticale and/or rye, may be added to the product formulation or protein composition.

The examples which follow are intended to illustrate individual aspects of the present invention, but are in no way to be understood as limiting.

EXAMPLES

I. Milling the Starch Feedstock

The millbases employed hereinbelow were produced as follows. Whole maize kernels were ground completely using a rotor mill. Using different beaters, milling paths or screen elements, three different degrees of fineness were obtained. A screen analysis of the millbase by means of a laboratory vibration screen (vibration analyzer: Retsch Vibrotronic type VE1; screening time 5 minutes, amplitude: 1.5 mm) gave the results listed in Table I.

TABLE I

| Experiment number | T 70/03 | T 71/03 | T 72/03 |
|---|---|---|---|
| <2 mm/% | 99.4 | 100 | 100 |
| <0.8 mm/% | 66 | 100 | 99 |
| <0.63 mm/% | 58.6 | 98.5 | 91 |
| <0.315 mm/% | 48.8 | 89 | 65 |
| <0.1 mm/% |  | 25 | 9.6 |
| <0.04 mm/% |  | 8 | 3.2 |
| Millbase in total | 20 kg | 11.45 kg | 13.75 kg |

II. Enzymatic Starch Liquefaction and Starch Saccharification

II.1.) Liquefaction in the Jet Cooker

To continuously liquefy a dry-milled maize meal, two stirred tanks having a volume of 250 l are set up; every hour, the maize meal which has been made into a slurry with water is fed alternately from each of them to the jet cooker. Typically, these tanks are set up in such a way that 117 kg of water are introduced, and an α-amylase, for example Termamyl SC, is added to the water in a concentration of 0.10% by weight (based on the amount of meal employed). Thereafter, 133 kg of maize meal are fed in at approx. 45° C. in a plurality of steps and mixed in. After adjusting a $Ca^{2+}$ concentration of 50 ppm, for example by adding $CaCl_2$, the pH is adjusted in a range of between 5.6 and 5.8. After all components have been added, the maize meal suspension is mixed thoroughly by stirring until it is used in the jet cooker. This suspension is then fed to the jet cooker at 250 kg/h at a pressure of 5 bar. Heating the maize meal suspension beyond the gelatinization temperature to 105° C. is accomplished by providing 25 kg/h steam in parallel (7.5 bar). In a tubular reactor with a holding time of 5 minutes, which is arranged downstream of the jet cooker, some of the gelatinized starch is broken down into dextrins (liquefaction 1). Thereafter, the temperature of the reaction mixture is reduced by flashing to 90° C., in which process approx. 5 kg/h of steam depart. Then, the second liquefaction is carried out at 90° C. in a further tubular reactor over a period of 100 minutes in order to fully break down the starch into dextrins. The resulting reaction mixture is then cooled to the saccharification temperature of 61° C. by renewed flashing, in which process approx. 14 kg/h water are lost.

II.1) Saccharification

A portion of the reaction mixture obtained in II.1) was saccharified in a random test. To this end, approx. 1000 g of the reaction mixture were transferred into a stirred tank and held at 61° C. with constant stirring. Stirring was continued during the entire duration of the experiment. After the pH had been adjusted to 4.3 using $H_2SO_4$, 17.9 g (15.2 ml) of Dextrozyme GA (Novozymes A/S) were added. The temperature was held for approximately 3 hours, during which process the course of the reaction was monitored by HPLC. At the end, the glucose concentration was 420 g/kg.

III. Strain

ATCC13032 lysC$^{fbr}$

In some of the following examples, a modified *Corynebacterium glutamicum* strain was employed, which had been described in WO 05/059144 under the name ATCC13032 lysC$^{fbr}$.

Example 1

Liquefied and saccharified maize meal hydrolyzate which had been prepared as described in protocol II was employed in shake-flask tests using *Corynebacterium glutamicum*.
Strain The modified wild type with feedback-deregulated aspartokinase ATCC13032 lysC$^{fbr}$ was used.
Preparation of the Inoculum The cells were streaked onto sterile CM+CaAc agar (composition: see Table 1; 20 minutes at 121° C.) and then incubated overnight at 30° C. The cells were subsequently scraped from the plates and resuspended in saline. 25 ml of the medium (see Table 2) in 250 ml Erlenmeyer flasks equipped with two baffles were inoculated in each case with such an amount of the cell suspension thus prepared that the optical density reached an $OD_{610}$ value of 0.5 at 610 nm.

TABLE 1

Composition of the CM + CaAc agar plates

| Concentration | Constituent |
|---|---|
| 10.0 g/l | D-glucose |
| 2.5 g/l | NaCl |
| 2.0 g/l | Urea |
| 5.0 g/l | Bacto peptone (Difco) |
| 5.0 g/l | Yeast extract (Difco) |
| 5.0 g/l | Beef extract (Difco) |
| 20.0 g/l | Casamino acids |
| 20.0 g/l | Agar |

Preparation of the Fermentation Liquor

The composition of the flask medium is listed in Table 2. The test was carried out in triple determination.

TABLE 2

Flask media

| Maize meal hydrolyzate | 143 g/l |
|---|---|
| $(NH_4)_2SO_4$ | 20 g/l |
| Urea | 5 g/l |
| $KH_2PO_4$ | 0.113 g/l |
| $K_2HPO_4$ | 0.138 g/l |
| ACES | 52 g/l |
| MOPS | 21 g/l |
| Citric acid × $H_2O$ | 0.49 g/l |
| 3,4-Dihydroxybenzoic acid | 3.08 mg/l |
| NaCl | 2.5 g/l |

TABLE 2-continued

| Flask media | |
|---|---|
| KCl | 1 g/l |
| MgSO$_4$ × 7 H$_2$O | 0.3 g/l |
| FeSO$_4$ × 7 H$_2$O | 25 mg/l |
| MnSO$_4$ × 4-6 H$_2$O | 5 mg/l |
| ZnCl$_2$ | 10 mg/l |
| CaCl$_2$ | 20 mg/l |
| H$_3$BO$_3$ | 150 mg/l |
| CoCl$_2$ × 6 H$_2$O | 100 µg/l |
| CuCl$_2$ × 2 H$_2$O | 100 µg/l |
| NiSO$_4$ × 6 H$_2$O | 100 µg/l |
| Na$_2$MoO$_4$ × 2 H$_2$O | 25 µg/l |
| Biotine (Vit. H) | 1050 µg/l |
| Thiamine × HCl (Vit B$_1$) | 2100 µg/l |
| Nicotinamide | 2.5 mg/l |
| Pantothenic acid | 125 mg/l |
| Cyanocobalamin (Vit B$_{12}$) | 1 µg/l |
| 4-Aminobenzoic acid (PABA; Vit. H$_1$) | 600 µg/l |
| Folic acid | 1.1 µg/l |
| Pyridoxin (Vit. B$_6$) | 30 µg/l |
| Riboflavin (Vit. B$_2$) | 90 µg/l |
| CSL | 40 ml/l |
| pH* | 6.85 |

*adjusted with dilute aqueous NaOH solution

After the inoculation, the flasks were incubated for 48 hours at 30° C. and with shaking (200 rpm) in a humidified shaker. After the fermentation was terminated, the glucose content and the lysine content were determined by HPLC. The HPLC analyses were carried out with an Agilent 1100 series LC system. The amino acid concentration was determined by means of high-pressure liquid chromatography on an Agilent 1100 series LC System HPLC. Pre-column derivatization with ortho-phthaldehyde permits the quantification of the amino acid formed; the amino acid mixture is separated using an Agilent Hypersil AA column.

Example 2

Liquefied and saccharified maize meal hydrolyzate which had been prepared by protocol II was employed in shake-flask experiments using *Aspergillus niger*.

Strain

An *Aspergillus niger* phytase production strain with 6 copies of the phyA gene from *Aspergillus ficuum* under the control of the glaA promoter was produced analogously to the preparation of NP505-7, which is described in detail in WO98/46772. A strain with 3 modified glaA amplicons (analogous to ISO505), but without integrated phyA expression cassettes, was used as the control.

Preparation of the Inoculum 20 ml of the preculture medium (see Table 3) in 100 ml Erlenmeyer flasks equipped with a baffle are inoculated with in each case 100 µl of a lyophilized culture and incubated for 24 h at 34° C. in a humidified shaker, with agitation (170 rpm).

TABLE 3

| Composition of the preculture medium | |
|---|---|
| Constituent | Concentration |
| Glucose | 30.0 g/l |
| Peptone from casein | 10.0 g/l |
| Yeast extract | 5.0 g/l |
| KH$_2$PO$_4$ | 1.0 g/l |
| MgSO$_4$ × 7 H$_2$O | 0.5 g/l |
| ZnCl$_2$ | 30 mg/l |
| CaCl$_2$ | 20 mg/l |

TABLE 3-continued

| Composition of the preculture medium | |
|---|---|
| Constituent | Concentration |
| MnSO$_4$ × 1 H$_2$O | 9 mg/l |
| FeSO$_4$ × 7 H$_2$O | 3 mg/l |
| Tween 80 | 3.0 g/l |
| Penicillin | 50 000 IU/l |
| Streptomycin | 50 mg/l |
| pH* | 5.5 |

*adjusted with dilute sulfuric acid 50 ml of the main culture medium (see Table 4) in 250 ml Erlenmeyer flasks equipped with a baffle are inoculated with in each case 5 ml of preculture.

Preparation of the Fermentation Liquor

The composition of the flask medium is listed in Table 4. Two flasks were set up with each sample.

TABLE 4

| Flask media | |
|---|---|
| Maize meal hydrolyzate | 166 g/l |
| Peptone from casein | 25.0 g/l |
| Yeast extract | 12.5 g/l |
| KH$_2$PO$_4$ | 1.0 g/l |
| K$_2$SO$_4$ | 2.0 g/l |
| MgSO$_4$ × 7 H$_2$O | 0.5 g/l |
| ZnCl$_2$ | 30 mg/l |
| CaCl$_2$ | 20 mg/l |
| MnSO$_4$ × 1 H$_2$O | 9 mg/l |
| FeSO$_4$ × 7 H$_2$O | 3 mg/l |
| Penicillin | 50 000 IU/l |
| Streptomycin | 50 mg/l |
| pH* | 5.6 |

*to be adjusted with dilute sulfuric acid

After the inoculation, the flasks were incubated in a humidified shaker for 6 days at 34° C. with agitation (170 rpm). After the fermentation had been stopped, the phytase activity was determined with phytic acid as substrate and at a suitable phytase activity level (standard: 0.6 U/ml) in 250 mM acetic acid/sodium acetate/Tween 20 (0.1% by weight), buffer pH 5.5. The assay was standardized for the application in microtiter plates (MTPs). 10 µl of the enzyme solution were mixed with 140 µl of 6.49 mM phytate solution in 250 mM sodium acetate buffer, pH 5.5 (phytate: dodecasodium salt of phytic acid). After incubation at 37° C. for one hour, the reaction was quenched by addition of an equal volume (150 µl) of trichloroacetic acid. One aliquot of this mixture (20 µl) was transferred into 280 µl of a solution comprising 0.32 NH$_2$SO$_4$, 0.27% by weight of ammonium molybdate and 1.08% by weight of ascorbic acid. This is followed by incubation for 25 minutes at 50° C. The absorption of the blue solution was measured at 820 nm.

The invention claimed is:
1. A process for the fermentative production of at least one organic compound having at least 3 C atoms or having at least 2 C atoms and at least 1 N atom, comprising the following steps:
   i) milling a starch feedstock, thus obtaining a millbase which comprises at least 10% by weight of the non-starchy solid constituents of the starch feedstock based on the starchy constituents of the millbase;
   ii) suspending the millbase in an aqueous liquid in such an amount that a dry-matter content in the suspension of at least 45% by weight results, iii) hydrolyzing the starchy constituent in the millbase by liquefaction and, if appropriate, subsequent saccharification, whereby an aqueous medium M is obtained with a sugar concentration of at least 35% by weight which comprises the hydrolyzed starchy constituents of the starch feedstock and at least 10% by weight of the nonstarchy solid constituents of the starch feedstock based on the amount of metabolizable sugar in the aqueous medium M; and iv) using the aqueous medium M obtained in step iii) in a fermentation for culturing a microorganism which is capable of overproducing the organic compound;

where, in step iii), the suspension obtained in step ii) is heated at temperatures above the gelatinization temperature of the starch present in the millbase by introducing steam into the suspension, wherein the organic compound is selected among the group consisting of mono-, di- and tricarboxylic acids, which optionally have hydroxyl groups attached to them and which have 3 to 10 carbon atoms; proteinogenic and nonproteinogenic amino acids; purine bases; pyrimidine bases; nucleosides; nucleotides; lipids; saturated and unsaturated fatty acids; diols having 4 to 10 carbon atoms; polyhydric alcohols having 3 or more hydroxyl groups; long-chain alcohols having at least 4 carbon atoms; carbohydrates; aromatic compounds; vitamins; provitamins; cofactors; nutraceuticals; proteins; carotenoids; ketones having 3 to 10 carbon atoms; lactones; biopolymers; and cyclodextrins; and wherein at least one starch-liquefying enzyme is added to the suspension before heating;

wherein cereal kernels are used as the starch feedstock.

2. The process according to claim 1, wherein the heating with steam is accomplished in a jet cooker.

3. The process according to claim 1, wherein the heated suspension of the millbase is cooled by flash evaporation to temperatures below the gelatinization temperature and the liquefaction of the starch is subsequently carried out in the presence of a starch-liquefying enzyme.

4. The process according to claim 1, wherein the hydrolysis of the starch comprises a saccharification step.

5. The process according to claim 1, additionally comprising the following steps:

v) culturing of the microorganism which is capable of overproducing the organic compound in an aqueous fermentation medium F which comprises metabolizable sugars; and vi) addition of the aqueous medium M to the fermentation medium F, during which process the hydrolyzed starchy constituents present in the aqueous medium M are metabolized by the microorganisms with formation of the organic compound.

6. The process according to claim 5, wherein the fermentation medium F, in step v), essentially comprises the aqueous medium M, the microorganisms which are capable of overproducing the organic compound, nutrient salts, conventional adjuvants and water for dilution.

7. The process according to claim 1, wherein the millbase employed in step ii) comprises at least 20% of the solid, nonstarchy constituents of the starch feedstock which are present in the starch feedstock.

8. The process according to claim 1, wherein the starch-liquefying enzyme is an α-amylase.

9. The process according to claim 1, wherein the microorganism employed for the fermentation is selected among the group consisting of natural or recombinant microorganisms which overproduce at least one of the following metabolites: enzymes, amino acids, vitamins, disaccharides, aliphatic mono- and dicarboxylic acids having 3 to 10 C atoms, aliphatic hydroxycarboxylic acids having 3 to 10 C atoms, ketones having 3 to 10 C atoms, alkanols having 4 to 10 C atoms, alkanediols having 3 to 8 C atoms and polyhydroxyalkanoates.

10. The process according to claim 9, wherein the microorganism is selected among those which overproduce one or more amino acids.

11. The process according to claim 9, wherein the microorganism is selected among those which overproduce one or more aliphatic mono- and dicarboxylic acids having 3 to 10 C atoms.

12. The process according to claim 9, wherein the microorganism is selected among those which overproduce one or more enzymes.

13. The process according to claim 12, wherein the microorganism is selected among those which overproduce a phytase.

14. The process according to claim 1, wherein the microorganism is selected among the group of genera consisting of *Corynebacterium, Bacillus, Ashbya, Escherichia, Aspergillus, Alcaligenes, Actinobacillus, Anaerobiospirillum, Lactobacillus, Propionibacterium, Clostridium,* and *Rhizopus.*

15. The process according to claim 14, wherein the microorganism is selected among strains of the genus *Corynebacterium.*

16. The process according to claim 1, wherein at least one microbial metabolite is depleted or isolated from the fermentation liquor and the volatile constituents of the fermentation liquor are subsequently substantially removed, a solid or semisolid protein composition being obtained.

17. The process according to claim 1, wherein at least some of the volatile constituents of the fermentation liquor are removed without previous isolation or depletion of a nonvolatile microbial metabolite and, if appropriate, without previous removal of solid constituents, a solid formulation of a nonvolatile microbial metabolite being obtained.

* * * * *